US010893028B2

(12) United States Patent
Dattolo et al.

(10) Patent No.: US 10,893,028 B2
(45) Date of Patent: Jan. 12, 2021

(54) SYSTEM AND METHOD FOR SECURE REMOTE CONTROL OF A MEDICAL DEVICE

(71) Applicant: DEKA Products Limited Partnership, Manchester, NH (US)

(72) Inventors: James J. Dattolo, Manchester, NH (US); Atlant G. Schmidt, III, Nashua, NH (US); Steven B. Meuse, Londonderry, NH (US); George W. Marchant, Jr., Goffstown, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 202 days.

(21) Appl. No.: 15/982,737

(22) Filed: May 17, 2018

(65) Prior Publication Data

US 2018/0375839 A1 Dec. 27, 2018

Related U.S. Application Data

(60) Provisional application No. 62/509,061, filed on May 20, 2017.

(51) Int. Cl.
*H04L 29/06* (2006.01)
*H04L 9/32* (2006.01)
(Continued)

(52) U.S. Cl.
CPC ........ *H04L 63/0442* (2013.01); *G06F 21/305* (2013.01); *G06F 21/606* (2013.01); *G16H 40/67* (2018.01); *G16H 80/00* (2018.01); *H04L 9/0656* (2013.01); *H04L 9/0869* (2013.01); *H04L 9/3236* (2013.01); *H04L 9/3271* (2013.01); *H04L 63/10* (2013.01);
(Continued)

(58) Field of Classification Search
CPC ... H04L 63/0442; H04L 63/10; H04L 9/0656; H04L 9/0869; H04L 9/3236; H04L 9/3271; G06F 21/305; G06F 21/606; H04W 12/04; H04W 12/08; G16H 40/67; G16H 80/00
See application file for complete search history.

(56) References Cited

U.S. PATENT DOCUMENTS

2015/0012057 A1* 1/2015 Carlson .............. A61N 1/37264
607/45
2016/0036949 A1* 2/2016 Holden ............... H04M 1/0254
455/557

OTHER PUBLICATIONS

Chang-Seop Park, "Security Mechanism Based on Hospital Authentication Server for Secure Application of Implantable Medical Devices", Jul. 24, 2014, BioMed Research International, vol. 2014, Article ID 543051 (Year: 2014).*

(Continued)

*Primary Examiner* — Noura Zoubair
(74) *Attorney, Agent, or Firm* — Kathleen Chapman

(57) ABSTRACT

A system and method for secure wireless control of a device including, but not limited to, replay attack protection, man-in-the-middle protection, data obfuscation, and challenge-response authentication. The system includes a control device, a controlled device interface, a controlled device, a control device interface, and a wireless link. The controlled device interface and the control device interface manage secure communications between the control device and the controlled device over the wireless link. The controlled device can include a medical device such as, for example, but not limited to, an insulin pump and a wheelchair.

16 Claims, 12 Drawing Sheets

(51) Int. Cl.
   *H04L 9/08*    (2006.01)
   *G06F 21/60*   (2013.01)
   *G16H 40/67*   (2018.01)
   *G16H 80/00*   (2018.01)
   *H04W 12/02*   (2009.01)
   *G06F 21/30*   (2013.01)
   *H04L 9/06*    (2006.01)
   *H04W 12/08*   (2009.01)
   *H04W 12/00*   (2009.01)
   *H04W 12/04*   (2009.01)
   *H04L 29/08*   (2006.01)

(52) U.S. Cl.
   CPC ....... *H04W 12/0013* (2019.01); *H04W 12/02* (2013.01); *H04W 12/0401* (2019.01); *H04W 12/08* (2013.01); H04L 63/0435 (2013.01); H04L 67/025 (2013.01); H04L 2209/88 (2013.01); H04W 12/001 (2019.01)

(56) References Cited

OTHER PUBLICATIONS

Rasmussen et al "Proximity-based Access Control for Implantable Medical Devices", in Proceedings of the 16th ACM Conference on Computer and Communications Security CCS'09, Nov. 9-13, 2009 (Year: 2009).*

Bluetooth Specification, "Core System Package, Specification of the Bluetooth System", Version 5.0, vol. 6, Dec. 6, 2016, pp. 2600-2648. (Year: 2016).*

Jae Dong Lee et al, "Service-Oriented Security Framework for Remote Medical Services in the Internet of Things Environment", Healthcare Informatics Research, Oct. 21, 2015, pp. 271-282 (Year: 2015).*

* cited by examiner

SYSTEM AND METHOD FOR SECURE REMOTE CONTROL OF A MEDICAL DEVICE

CROSS REFERENCE TO RELATED APPLICATIONS

This application claims the benefit of U.S. Provisional Application Ser. No. 62/509,061, filed May 20, 2017, entitled SYSTEM AND METHOD FOR SECURE REMOTE CONTROL OF A MEDICAL DEVICE, which is incorporated herein by reference in its entirety.

BACKGROUND

The present teachings relate generally to remote control of a device, and more specifically to remote control of medical devices.

A wide range of products are known for remote control of devices. From toys to useful devices for daily living, remote control and monitoring have become standards in many industries. Early remote control devices relied on line-of-sight communications between the controller and the controlled device. More recently, remote control of devices can be largely carried out by a combination of computer applications and wired or wireless communications networks. In particular, cellular phones can control and monitor a host of devices. Remote control of medical devices, however, can include therapy delivery timing and security/privacy issues that could be unnecessary for the typical remotely-controlled devices.

What is needed is a system that can enable secure communications with and secure control of a device such as, for example, a medical device. The communications can be wireless. The control device can include any kind of electronic device that can accommodate a communications protocol that is compatible with a communications protocol executing in the medical device.

SUMMARY

The secure remote control apparatus and method of the present teachings can enable secure communications between a control device and a controlled device, and can enable secure control of the controlled device.

A method for securely remotely controlling a device such as, for example, a medical device can include, but is not limited to including, configuring a communications system between a control device and the medical device. The communications system can include a control communications state machine and a medical device communications state machine. The control communications state machine can include a current control communications state, and the medical device communications state machine can include a current medical device communications state. The method can include configuring a control messaging system at the control device. The control messaging system can include at least one control state machine, and the at least one control state machine can include a current control state. The method can include configuring a medical device messaging system at the medical device. The medical device messaging system can include at least one medical device state machine, and the medical device state machine can include a current medical device state. The method can include preparing a device-specific message based on the current medical device state. The device-specific message can be formatted according to a second protocol, and the second protocol can include a second plurality of message types. The second plurality of message types can be specific to the medical device. The method can include preparing a communications message based on the current control state. The communications message can be formatted according to a first protocol, and can include the device-specific message. The first protocol can include a first plurality of message types, and the first plurality of message types can be generic to a plurality of devices.

The method can include queuing, by the control device, the communications message based on the current control state, and dequeuing, by the control communications system, based on the current control device communications state, the communications message. The method can include applying, by the control communications system, communications threat control to the communications message and transmitting, by the control communications system, based on the current control communications state, the threat controlled communications message. The method can include receiving, by the medical device communications system, based on the current medical device communications state, a message, and verifying, by the medical device communications system, based on the communications threat control and the current medical device state, that the received message is the same as the communications message. The method can include queuing, by the medical device communications system, the verified message, dequeuing, by the medical device, based on the current medical device state, the verified message, and controlling the medical device based on the device-specific message and the current medical device state.

The communications system can optionally include wireless communications between the control device and the medical device. The first protocol can optionally include a remote interface specification (RIS) protocol. The second protocol can optionally include a service component architecture (SCA) protocol. The communications threat control can optionally include clear text data obfuscation and clear text data deobfuscation. The clear text data obfuscation can optionally include generating a random byte, using the random byte as a random key, transforming the random key into a count of random bytes in a known range, generating the number of random bytes that equals the count, and transforming several of the random bytes into a linear feedback shift register (LFSR) seed value. The method clear text data obfuscation further can optionally include whitening an input counted string using the LFSR seed value. The clear text data deobfuscation can optionally include transforming a random key into a count of random bytes in a known range, transforming at least one of the random bytes into a LFSR seed value, dewhitening the counted string byte count value, and dewhitening the counted string using the byte count value. The communications threat control can optionally include a challenge-response process. The challenge-response authentication process can optionally include picking, by a transmitting entity, a large random number, sending, by the transmitting entity, the large random number to a receiver, transforming, by the transmitting receiving entity and by a receiving entity, the large random number according to an algorithm known to the transmitting entity and the receiving entity, cryptographically securely processing, by the transmitting entity and the receiving entity, the transformed number, creating a receiver processed number and a transmitter processed number, sending, by the receiving entity, the receiver processed number, receiving, by the transmitting entity, the receiver processed number, and checking, by the transmitting entity, that the receiver processed number and the transmitter processed number are equal. The cryptographically secure processing can optionally include hashing and encryption.

A system for securely remotely controlling a medical device can include, but is not limited to including, a configuration processor configuring a communications system between a control device and the medical device. The communications system can include a control communications state machine and a medical device communications state machine. The control communications state machine can include a current control communications state. The medical device communications state machine can include a current medical device communications state. The configuration processor can configure a control messaging system at the control device, and the control messaging system can include at least one control state machine. The at least one control state machine can include a current control state. The configuration processor can configure a medical device messaging system at the medical device, and the medical device messaging system can include at least one medical device state machine. The at least one medical device state machine can include a current medical device state.

The system can include a message processor that can prepare a device-specific message based on the current medical device state. The device-specific message can be formatted according to a second protocol, and the second protocol can include a second plurality of message types. The second plurality of message types can be specific to the medical device. The message processor can prepare a communications message based on the current control state, and the communications message can be formatted according to a first protocol. The communications message can include the device-specific message. The first protocol can include a first plurality of message types, and the first plurality of message types can be generic to a plurality of devices. The message processor of the control device can queue the communications message based on the current control state. The message processor of the control communications system can dequeue, based on the current control device communications state, the communications message, and the control communications system can apply communications threat control to the communications message.

The system can include a communications processor that can transmit, by the control communications system, based on the current control communications state, the threat controlled communications message. The communications processor can receive, by the medical device communications system, based on the current medical device communications state, a message. The system can include a threat processor that can verify, by the medical device communications system, based on the communications threat control and the current medical device state, that the received message is the same as the communications message. The threat processor of the medical device communications system can queue the verified message. The system can include a control processor that can dequeue, by the medical device, based on the current medical device state, the verified message. The control processor can control the medical device based on the device-specific message and the current medical device state.

The communications system can optionally include wireless communications between the control device and the medical device. The first protocol can optionally include a remote interface specification protocol. The second protocol can optionally include a SCA protocol. The communications threat control can optionally include clear text data obfuscation and clear text data deobfuscation. The clear text data obfuscation can optionally include a first process generating a random byte, using the random byte as a random key, transforming the random key into a count of random bytes in a known range, generating the number of random bytes that equals the count, and transforming several of the random bytes into a linear feedback shift register (LFSR) seed value. The first process can optionally include whitening an input counted string using the LFSR seed value. The clear text data deobfuscation can optionally include a second process transforming a random key into a count of random bytes in a known range, transforming at least one of the random bytes into a LFSR seed value, dewhitening the counted string byte count value, and dewhitening the counted string using the byte count value. The communications threat control can optionally include a challenge-response authentication. The challenge-response authentication can optionally include a third process that can pick, by a transmitting entity, a large random number, and can send, by the transmitting entity, the large random number to a receiver. The third process can transform, by the transmitting entity and by a receiving entity, the large random number according to an algorithm known to the transmitting entity and the receiving entity. The third process can cryptographically securely process, by the transmitting entity and the receiving entity, the transformed number, and can create a receiver-processed number and a transmitter-processed number, sending, by the receiving entity, the receiver processed number. The third process can receive, by the transmitting entity, the receiver processed number, and can check, by the transmitting entity, that the receiver processed number and the transmitter processed number are equal.

A method for securely remotely controlling a medical device with a control device, where the medical device and the control device can be coupled by a communications link, and where the control device can include a control messaging system, and where the medical device can include a medical device messaging system, can include, but is not limited to including, preparing a device-specific message based on a current medical device state of the medical device. The device-specific message can be prepared by the medical device messaging system that can include at least one medical device state machine. The at least one medical device state machine can include the current medical device state. The device-specific message can be formatted according to a second protocol that can include a second plurality of message types. The second plurality of message types can be specific to the medical device. The method can include preparing a communications message based on a current control state. The communications message can be prepared by the control messaging system that can include at least one control state machine that can include the current control state. The communications message can be formatted according to a first protocol, and can include the device-specific message. The first protocol can include a first plurality of message types that can be generic to a plurality of devices. The method can include queuing, by the control device, the communications message based on the current control state, and dequeuing, by the control communications system, the communications message based on the current control device communications state. The method can include applying, by the control communications system, communications threat control to the communications message, and transmitting, by the control communications system, the threat controlled communications message based on the current control communications state. The method can include receiving, by the medical device communications system, a message based on the current medical device communications state, and verifying, by the medical device communications system, based on the communications threat control and the current medical device state, that the received message is the same as the threat controlled communications message. The method can include queuing, by the medical device communications system, the verified received message, dequeuing, by the medical device, based on the current medical device state, the verified received message, and controlling the medical device based on the device-specific message included in the verified received message and the current medical device state. The clear text data obfuscation can optionally include generating a random byte, using the random byte as a random key, transforming the random key into a count of random bytes in a known range, generating the number of random bytes that equals the count, and transforming several of the random bytes into a linear feedback shift register (LFSR) seed value. The clear text data obfuscation can optionally include whitening an input counted string using the LFSR seed value. The clear text data deobfuscation can optionally include transforming a random key into a count of random bytes in a known range, transforming at least one of the random bytes into a LFSR seed value, dewhitening the counted string byte count value, and dewhitening the counted string using the byte count value. The communications threat control comprises a challenge-response authentication process. The challenge-response authentication process can optionally include picking, by a transmitting entity, a large random number, sending, by the transmitting entity, the large random number to a receiver, transforming, by the transmitting entity and by a receiving entity, the large random number according to an algorithm known to the transmitting entity and the receiving entity, cryptographically securely processing, by the transmitting entity and the receiving entity, the transformed number, creating a receiver processed number and a transmitter processed number, sending, by the receiving entity, the receiver processed number, receiving, by the transmitting entity, the receiver processed number, and checking, by the transmitting entity, that the receiver processed number and the transmitter processed number are equal. The cryptographically secure processing can optionally include hashing and/or encryption.

BRIEF DESCRIPTION OF THE DRAWINGS

The present teachings will be more readily understood by reference to the following description, taken with the accompanying drawings, in which.

DETAILED DESCRIPTION

The system of the present teachings can enable secure communications with and secure control of a device such as, for example, a medical device, wirelessly through any kind of electronic device that can accommodate a wireless protocol. The wireless protocol can include, but is not limited to including, the BLUETOOTH® protocol. For example, an electronic device such as, for example, a cell phone or an IPAD® device can include support for a wireless protocol. The controlled device, for example, the medical device, can also include support for the same wireless protocol. The system can include devices methods for securing communications between the controlling device and the controlled device.

Figure 1:
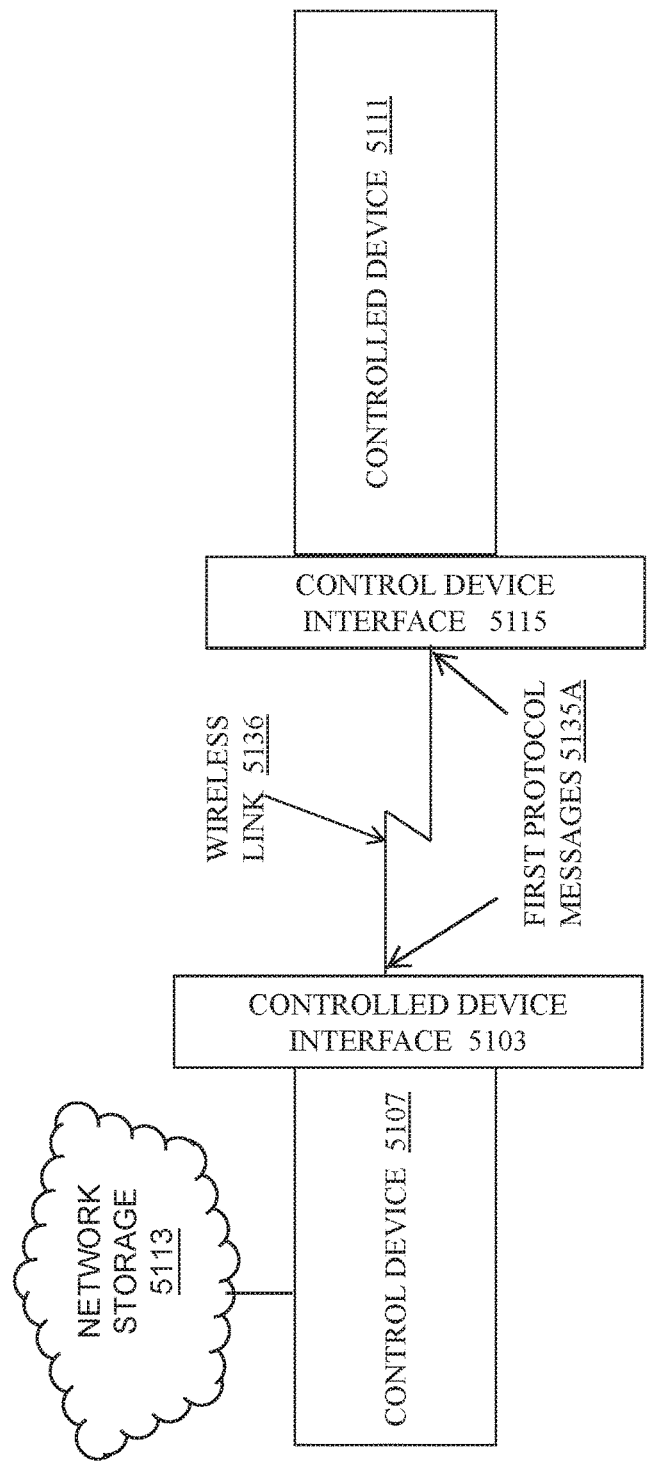
FIG. 1 is a schematic block diagram of the system of the present teachings.
Figure 2:
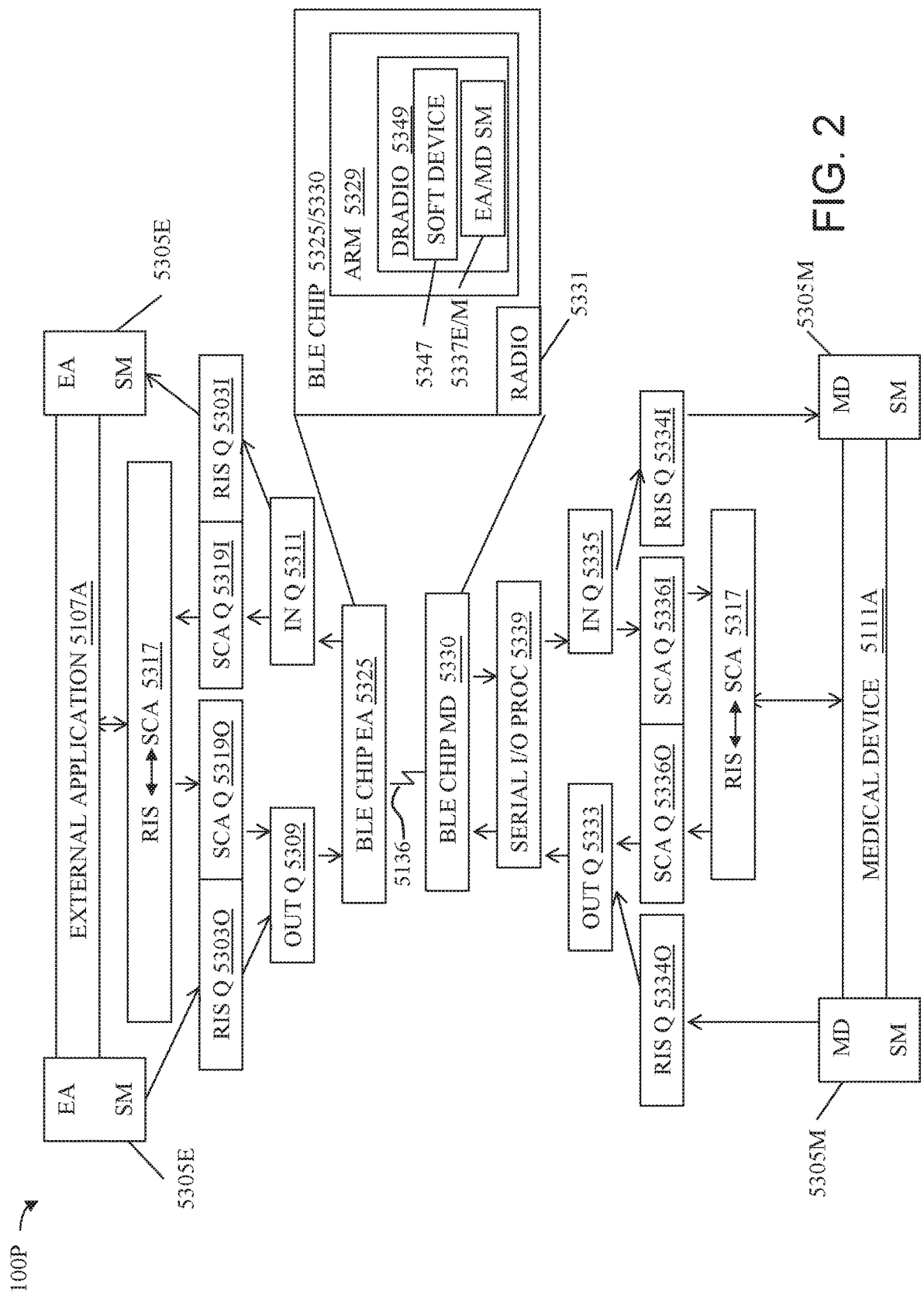
FIG. 2 is a schematic block diagram of the first configuration of the control device of the present teachings.

Referring now primarily to FIG. 1, remote control of a medical device can be enabled by secure communications between control device 5107 and controlled device 5111, for example, but not limited to, medical device 5111A (FIG. 2). Control device 5107 can include, but is not limited to including, a cell phone, a personal computer, and a tablet-based device, and is also referred to herein as an external device, a configuration of which can include external application 5107A (FIG. 2). Control device 5107 can include voice recognition that can be used to control controlled device 5111. Control device 5107 and controlled device 5111 can communicate using a first protocol tunneling a second protocol, and, for example, a wireless protocol such as, for example, but not limited to, the BLUETOOTH® Low Energy (BLE) protocol. Control device 5107 can execute external applications that can enable wireless control of controlled device 5111. Communications between control device 5107 and controlled device 5111 can include, but are not limited to including, securely pairing local and remote radios associated with control device 5107 and controlled device 5111, encrypting traffic across the local and remote radios, filtering pre-selected devices from the list of advertising peripheral radios, and whitelisting pre-selected paired radios for streamlining the scan/pair/connect sequence. Control device 5107 can enable user selection of one of a group of advertising devices, and can enable communications with network storage 5113. Data from controlled device 5111, such as, for example, but not limited to, event logs, can be requested by control device 5107 and uploaded to network storage 5113. In some configurations, control device 5107 can listen for the notification of new data and can determine if the new data are to be uploaded to network storage 5115. Any data that are to be uploaded can be queued for transmission to network storage 5113. In some configurations, if control device 5107 is connected to a WiFi network, control device can attempt to upload any data that is not currently residing in network storage 5113. In some configurations, if control device 5107 is connected to a cell network, or network storage 5113 is not reachable, control device 5107 can queue the data and attempt to send it when the network status changes. In some configurations, the data can be deleted from control device 5107 and controlled device 5111 when network storage 5113 confirms that the data have been received and/or stored successfully. In some configurations, data can include event log data and raw data generated by controlled device 5111. Controlled device interface 5103 can include, but is not limited to including, data structures that can represent the state of controlled device interface 5115. In some configurations, data can be maintained for a pre-selected amount of time. In some configurations, after the pre-selected amount of time, the data can be deleted if, for example, there is insufficient space on control device 5107. In some configurations, the data can be purged in priority order with low priority events purged before medium priority events. Medium priority data can be purged before high priority data. In some configurations, engineering events can be low priority and removed first, device events can be medium priority and removed if low events and/or other low priority data have already been removed, and therapy events can be high priority and removed if space is needed. Control device 5107 can provide view controllers that can support device registration and device association of network storage 5113. Control device 5107 can provide the ability to determine if a device is registered and associated with network storage 5113.

Continuing to refer primarily to FIG. 1, external application 5107A (FIG. 2) can simulate operation of controlled device interface 5103, and can enable a workflow that can assist the user in setting up and changing information about controlled device interface 5103. External application 5107A (FIG. 2) can provide user selection of controlled device interface 5103 that can advertise an available wireless connection. External application 5107A (FIG. 2) can include initial setup of controlled device interface 5103 that can include accessing and sending configuration parameters to controlled device interface 5103 including date and time, alert/alarm notification settings, and configuration options. Initial setup can include configuring a communications interface to communicate with network storage 5113. If controlled device 5111 is, for example, an insulin pump, external application 5107A (FIG. 2) can include storing and editing basal patterns, and managing insulin delivery. Managing insulin delivery can include, but is not limited to including, starting basal delivery, stopping basal delivery, starting a temporary basal modification, for example, as a fixed rate or a percentage change, stopping a temporary basal modification, starting a manual bolus delivery as, for example, a normal, extended, or dual bolus, starting a preset bolus delivery as, for example, a normal, extended, or dual bolus, starting a bolus delivery after calculating a suggested bolus using the calculations defined in the bolus calculator description as a normal, extended, or dual bolus, and stopping a bolus delivery. External application 5107A (FIG. 2) can provide visibility into events happening on controlled device 5111 including providing the ability to retrieve event data from controlled device interface 5103 and providing a view of data that are relevant to therapeutic decisions. These data can be stored in third configuration control device 107A (FIG. 3) and can include, in the case of an insulin pump, basal delivery changes, bolus deliveries, settings changes, bolus calculations, alarms and alerts, and daily totals. External application 5107A (FIG. 2) can retain data destined for network storage 5113 until wireless communications link 5136 is available. External application 5107A (FIG. 2) can remind the user to, for example, check blood glucose level at pre-selected times, and to perform a bolus within a specified window of time.

Referring now to FIG. 2, wireless communications system 100P can enable control of controlled device 5111 (FIG. 1), for example, but not limited to, medical device 5111A, through, for example, but not limited to, external application (EA) 5107A executing on control device 5107 (FIG. 1) (a cell phone, a PC, or a tablet, for example). In some configurations, a user interface means associated with medical device 5111A can include support for wireless communications to/from medical device 5111A. Medical device 5111A and external application 5107A can accommodate a user interface executing as part of external application 5107A that can, for example, override the commands generated by the user interface means associated with medical device 5111A. For example, a virtual joystick executing as a part of external application 5107A can override the commands of the physical joystick associated with a wheelchair. Medical device 5111A and external application 5107A can decode and use the messages moving between them. Wireless communications system 100P can include, but is not limited to including, protocol conversion processes 5317, input queues 5311/5335, output queues 5309/5333, state machines 5305E and 5305M, and wireless processors 5325/5330. Protocol conversion processes 5317 can feed SCA output queues 5319O/5336O and RIS output queues 5334O/5303O with messages generated by external application 5107A and medical device 5111A. Protocol conversion processes 5317 can receive messages from SCA input queues 5319I/5336I and RIS input queues 5334I/5303I that have received messages input queues 5311/5335. Input queues 5311/5355 can feed SCA input queues 5319I/5336I and RIS input queues 5334I/5303I with messages received from external application BLE chip 5325 and medical device BLE chip 5330 (through serial I/O processor 5339). Output queues 5309/5333 can feed external application BLE chip 5325 and medical device BLE chip 5330 (through serial I/O processor 5339). Medical device state machine 5305M can manage the process of communicating wirelessly from the perspective of medical device 5111A. External application state machine 5305E can manage the process of communicating wirelessly from the perspective of external application 5107A. In particular, both medical device state machine 5305M and external application state machine 5305E can manage the entry and exit of states from which messages can be generated and sent and/or received according pre-selected protocols. The messages can, for example, direct medical device 5111A and/or external application 5107A to respond to a status of dradio 5349. External application wireless processor 5325 can execute on control device 5107 (FIG. 1) and can communicate with external application 5107A. Medical device wireless processor 5330 can execute on medical device 5111A and can communicate with components of medical device 5111A.

Continuing to refer to FIG. 2, both external application wireless processor 5325 and medical device wireless processor 5330 can include a processor, for example, but not limited to, advanced RISC machine (ARM) processor 5329, that can execute wireless control code, termed herein, for convenience, dradio 5349. In some configurations, the processor can include, but is not limited to including, state machines that can manage the radio and can add functionality to a wireless communications transport layer. In some configurations, the processor can control a BLUETOOTH® soft device such as, for example, but not limited to, a Nordic Semiconductor S1x0 SoftDevice. Dradio 5349 executing on control device 5107 (FIG. 1) can include at least one external application radio state machine 5305E, and dradio 5349 executing on medical device 5111A can include at least one medical device radio state machine 5305M. At least one radio state machine can manage the states of I/O to soft device 5347. Soft device 5347 can include a wireless protocol processor such as, for example, but not limited to, a processor that communicates using the BLE protocol.

Continuing to refer to FIG. 2, the BLE protocol covers the four lowest layers and associated protocols defined by the BLUETOOTH® specification (Specification of the BLUETOOTH® System, Dec. 2, 2014, https://www.bluetooth.org/en-us/specification/adopted-specifications). BLE devices operate in the unlicensed 2.4 GHz Industrial Scientific Medical band. Radio frequency (RF) channels are defined in the 2.4 GHz industrial, scientific, and medical (ISM) band, and the RF channels are allocated into two BLE physical channels: advertising and data. The advertising physical channel uses three RF channels for discovering devices, initiating a connection and broadcasting data. The data physical channel uses up to 37 RF channels for communication between connected devices. The BLE includes a link layer that uses one physical channel at a time. The link layer has one packet format used for both advertising channel packets and data channel packets. All packets can include a cyclic redundancy check (CRC). Data whitening is used to avoid long sequences of zeros or ones, e.g. 0000000b or 1111111b, in the data bit stream and is performed after the CRC in the transmitter. De-whitening is performed before the CRC in the receiver. A linear feedback shift register (LFSR) can be used to generate a de-whitening value. Each byte in the input string is exclusively OR'd with the de-whitening value, and the result is saved in a counted output string. The link layer may perform device filtering based on the device address of the peer device. Link layer device filtering is used by the link layer to minimize the number of devices to which it responds. The set of devices that the link layer uses for device filtering is called the white list.

Continuing to refer to FIG. 2, to comply with the BLE protocol, standby, advertising, scanning, initiating, and connection states must be available. Advertising state includes transmitting advertising packets and listening for responses. Scanning state includes listening for packets from advertising devices. Initiating state includes listening for advertising from specific devices and initiating connections. A connection is considered to be established when a data channel packet has been received from the peer device. When two devices are in a connection, one device acts as a master, the other as a slave. If the connection state is entered from the initiating state, the device entering the connection state becomes the master. If the connection state is entered from advertising state, the device entering the connection state becomes the slave. The master controls the timing of a connection event. A connection event is a point of synchronization between the master and the slave. The link layer can enable the encryption of packets after entering the connection state.

Continuing to refer to FIG. 2, both external application radio state machine 5305E and medical device radio state machine 5305M can manage the states of radios 5331, and can provide information about radios 5331 to external application 5107A and medical device 5111A. Dradio 5349 can include general-purpose functionality and customized services to support medical device 5111A, for example. Medical device 5111A can be customized for users of varying abilities and physical characteristics, and a training mode can be configured for new users. Medical device 5111A can be remotely controlled for stowage, and parametric and performance data can be downloaded to medical device 5111A. When medical device 5111A enters a wireless-enabled mode, external application 5107A can send commands to medical device 5111A and can receive the corresponding responses. External application 5107A and medical device 5111A can create, for example, but not limited to, first protocol messages 5135A (FIG. 1) formatted according to a first protocol such as, for example, but not limited to, the remote interface specification (RIS) protocol (see FIG. 4A), to communicate information to processors of medical device 5111A, and vice versa. External application 5107A and medical device 5111A can create, for example, but not limited to, messages formatted according to a second protocol such as, for example, but not limited to, the SCA protocol (see FIG. 4B), to communicate control commands and data to processors of medical device 5111A. The second protocol can be extensible to accommodate various types of controlled devices 5111 (FIG. 1) and various functions available through external application 5107A. For example, a radio-control application executing on an IPOD® device can exchange messages with medical device 5111A by using, for example, but not limited to, messages following the RIS protocol (see FIG. 4A), and can send virtual device commands to medical device 5111A by using, for example, but not limited to, messages following the SCA protocol (see FIG. 4B).

Continuing to refer to FIG. 2, at the user's command, dradios 5349 can, through state machines 5305E/M and soft device 5347, cooperate to scan for peripheral radios, choose one that is advertising its readiness to communicate, and initiate a wireless session with the desired peripheral radio, for example, but not limited to, the peripheral radio of medical device 5111A. If BLUETOOTH® communications are used, radio 5331 and soft device 5347 can provide BLUETOOTH® central radio functionality required to set up and maintain communications between medical device 5111A and control device 5107 (FIG. 1). In some configurations, external applications 5107A executing on ANDROID® devices and iOS devices can use a wireless mechanism internal to ANDROID® devices or iOS devices to communicate with medical device 5111A. External application state machine 5305E can set up, control, and monitor wireless chip 5325 in a particular mode, such as, for example, central radio mode.

Continuing to refer to FIG. 2, dradio 5349 can manage radio 5331 through functionality such as, for example, but not limited to, sending messages and responses to command and interrogate radio 5331, sending data over wireless link 5136, securely pairing remote radios 5331, encrypting radio traffic, filtering pre-selected devices from the list of advertising peripheral radios, and whitelisting the last-paired remote radios 5331, which can assist with the scan/pair/connect sequence. With respect to medical device 5111A, state machine 5305M can manage radio 5331, serial I/O processor 5339 can provide low-level, thread-safe serial I/O support, and RIS-SCA process 5317 can extract/embed SCA messages from/in RIS protocol payloads. In some configurations, RIS-only messages that are transmitted/received by radio 5331 can be discarded by external application wireless state machine 5305E or controlled device interface 5103 (FIG. 1). Encapsulated SCA messages, for example, but not limited to, commands and status requests, can be placed upon SCA output queue 5319O for transfer to output queue 5309. To support various types of controlled devices 5111 (FIG. 1), RIS messages specific to a particular type of controlled devices 5111 (FIG. 1) can augment a basic set of RIS messages. For incoming data packets, SCA messages can be extracted from incoming RIS messages, and the messages can be dispatched to thread-safe, circular queues for consumption by external application 5107A or medical device 5111A. Outgoing messages can be queued separately depending on whether they are RIS or SCA messages. RIS messages that originate with external application 5107A can be placed on RIS output Q 5303O and moved to output queue 5309 when a queue slot is available. RIS-SCA process 5317 can retrieve SCA messages from RIS messages and vice versa to maintain transparency to SCA-aware software in system 100P.

Continuing to refer to FIG. 2, in some configurations, the encapsulation of messages formatted in the second protocol within messages formatted in the first protocol can enable flexible communications between medical device 5111A and external application 5107A. External application 5107A can receive information from, for example, a user, and the information can be translated into second protocol messages that can then be encapsulated in first protocol messages and transmitted to medical device 5111A. Wireless state machines 5305E/M can include software constructs that can manage the states of wireless processors 5325/5330. State machines 5305E/M can maintain the synchronization of peripheral and central radio states of medical device 5111A and external application 5107A.

Figure 3:
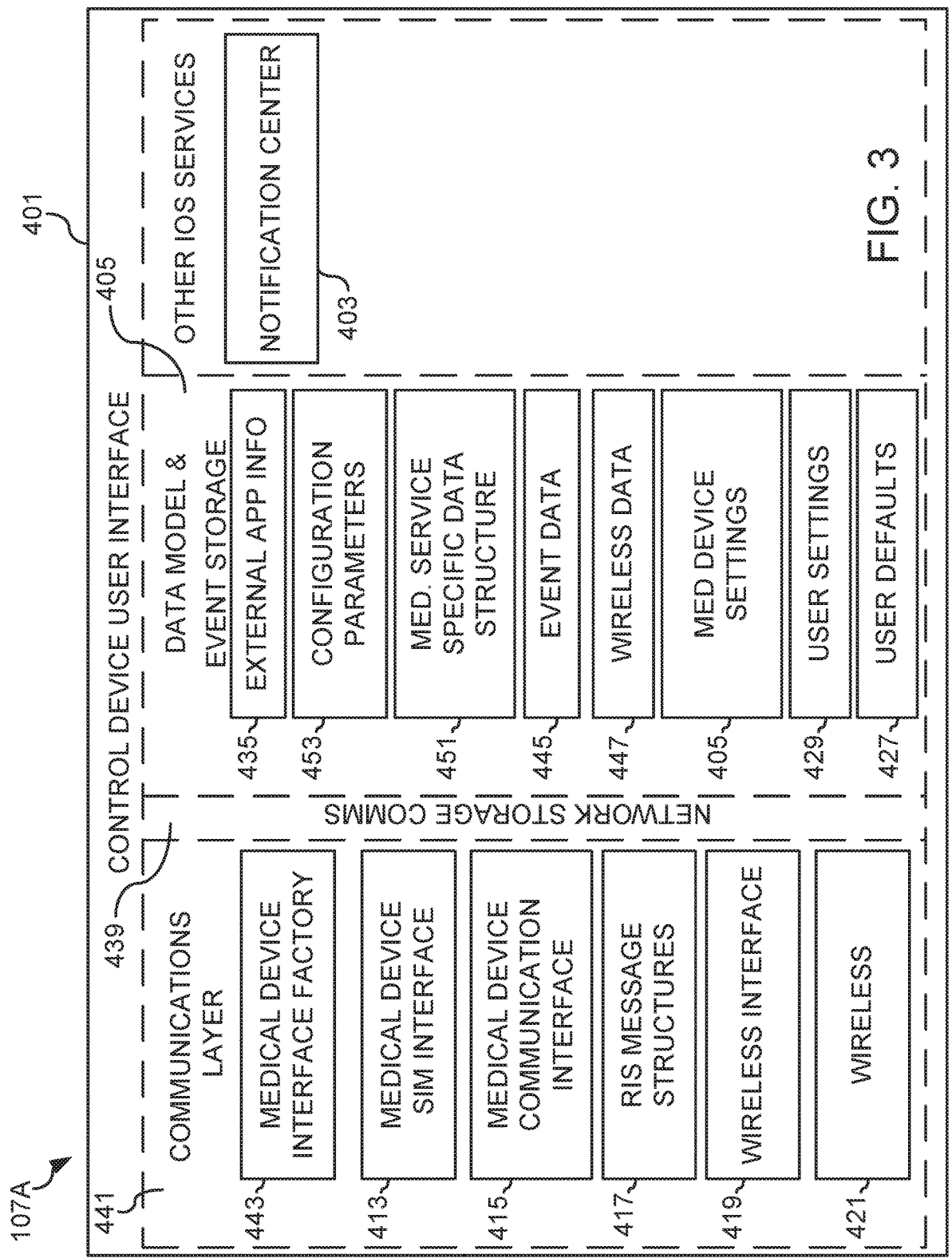
FIG. 3 is a schematic block diagram of the second configuration of the system of the present teachings.
Figure 4A:
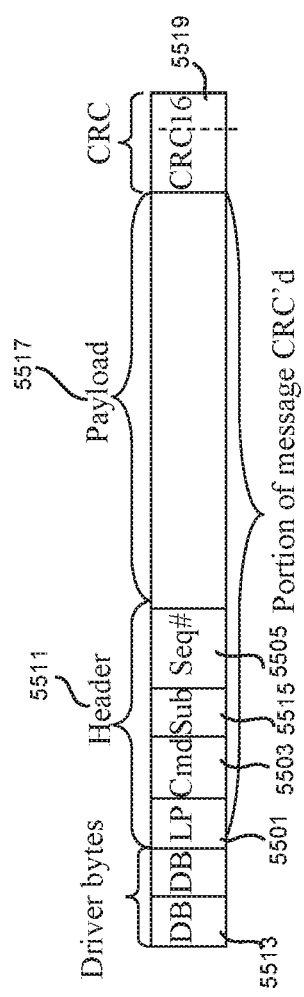
FIG. 4A is a schematic block diagram of the message format of a first configuration of a first protocol message of the present teachings.

Referring now to FIG. 3, third configuration control device system 107A can include a control device executing an external application in the iOS mobile operating environment, for example, and a controlled device such as, for example, a medical pump. The external application can remotely control a medical device such as, for example, but not limited to, the medical pump, and can include communications layer 441, networked storage communications 439, data model and event storage means 405, and other services. Services that can be provided by the iOS operating system can include user interface services, graphics services, object-to-object communications and management means, wireless communications framework, and data persistence means. Control device user interface 401 can include class and controller class view means and story boards that can interface with iOS user interface services and graphics services. Communications layer 441 can include, for example, medical device interface 443, medical device subscriber interface 413, medical device communication interface 415, RIS message structures 417, and wireless interface layer 419 that can interface with the operating system wireless layer 421. Medical device communications can occur at wireless interface layer 419 and medical device communication interface layer 415 levels. Wireless interface layer 419 can manage the passing of data and the callbacks generated when data are received from the medical device through wireless stack 421. Medical device communication interface layer 415 can create an interface ensuring messages are correct, complete, and adhere to RIS protocol (FIG. 4A). Wireless interface layer 419 can manage the connecting and transmission of byte data across wireless layer 421. Data model and event data storage 405 can include external application information 435, configuration parameters 453, medical device-specific settings 451, and event data 445 that can interface with iOS notification means 403. Data model and event data storage 437 can include iOS persistent data such as medical device-specific settings 451, user defaults 427, and user settings 429.

Referring now to FIG. 4A, the first protocol can support communications between control device 5107 (FIG. 1) that can be physically remote from control device interface 5115 (FIG. 1). In some configurations, the first protocol can include the RIS protocol in which each message can include header 5511, payload 5517, and data check 5519. Messaging systems executing on control device 5107 (FIG. 1) and control device interface 5115 (FIG. 1) can parse header 5511 and verify data check section 5519. Header 5511 can include, but is not limited to including, length of payload 5501, command 5503, sub-command 5515, and sequence number 5505. Sequence number 5505 can be incremented for each new message sent. Data check section 5519 can include, but is not limited to including, a CRC of header 5511 and payload 5517. The first protocol can include, but is not limited to including, messages that can vary in length. Messages can include header 5511, payload 5517, and CRC 5519. Control device interface 5115 (FIG. 1) can require that certain messages be available in the first protocol to support remote control of controlled device 5111 (FIG. 1). The first protocol can transparently tunnel messages formatted in a second protocol and encapsulated within messages formatted according to the first protocol for transmission and reception over, for example, wireless link 5136 (FIG. 2). Devices that communicate using the second protocol can be compatible with any updates that might happen in the wireless protocol and/or first protocol and can require no changes to operate seamlessly. Likewise, various types of medical devices can be controlled by using a generic shell protocol such as the RIS protocol that can surround the medical device-specific protocol and/or message set such as the SCA protocol.

Continuing to refer primarily to FIG. 4A, communications device drivers can provide driver bytes 5513 before message header 5511 that can be used by, for example, a serial peripheral interface (SPI) and remote communications drivers. Messages can be identified by the combination of command 5503 and sub-command 5515. Each command 5503 and sub-command 5515 pair specifies the specific format and intent of the message. Sub-command 5515 can include a response bit that can indicate that the message is a response to command 5503. When a packet is received which passes the CRC validation, a response will be sent. All response messages will have the response bit of sub-command 5515 set. In some configurations, sequence number 5505 of the response message must match sequence number 5505 of the original message. If the message is not a valid command, or the command cannot currently be processed by the system, the response will be a negative acknowledgement with a code to indicate the reason the message is considered invalid or inoperable. Messages that fail CRC validation or unexpected message responses can be dropped and treated the same as any message lost during transport. The application code performing the send on the source node can be responsible for generating a timeout, performing retries and ultimately self-generating a dropped message negative acknowledgement response in the case of dropped messages. Control device interface 5111 (FIG. 1) and controlled device interface 5103 can detect and react to communications issues such as, for example, but not limited to, CRC inconsistencies, timeouts, and therapy number inconsistencies.

Continuing to refer to FIG. 4A, in some configurations, a maximum message length can be imposed that may not include driver bytes 5513. If controlled device 5111 (FIG. 1) is a medical device, messages can include therapy commands that can include therapy number 5613 (FIG. 7) in payload 5517. In some configurations, a next therapy number can be provided in either a status message or a response. Therapy commands can be rejected if controlled device 5111 (FIG. 1) has not been configured for therapy. Therapy commands can be rejected by controlled device 5111 (FIG. 1) if therapy number 5613 (FIG. 7) is not valid.

Continuing to still further refer to FIG. 4A, first protocol CRC 5519 can be computed over header 5511 and payload 5517. When a message is received that has passed CRC validation, a response message can be sent. In some configurations, if the message does not include a valid command 5503, or command 5503 cannot currently be processed by the system, the response can include a negative acknowledgement that can have a code that can indicate the reason the message is considered invalid or inoperable. Messages that fail CRC validation or unexpected message responses can be dropped and treated the same as any message lost during transport. Controlled device interface 5103 (FIG. 1) and control device interface 5115 (FIG. 1) can both perform source node functions because they can each be the originator of and/or conduit for source messages. Whichever of controlled device interface 5103 (FIG. 1) or control device interface 5115 (FIG. 1) sends the message can generate a timeout if necessary, perform message send retries, if necessary, and self-generate a dropped message negative acknowledgement response if a dropped message is detected.

Figure 4B:
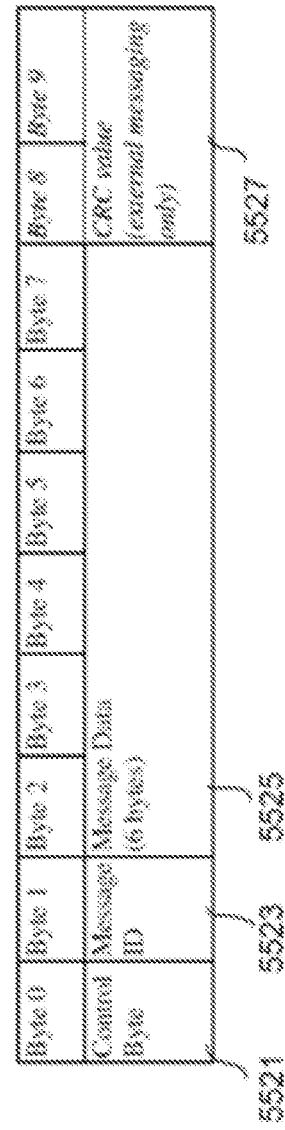
FIG. 4B is a schematic block diagram of the message format of a first configuration of a second protocol message of the present teachings.

Referring now to FIG. 4B, controlled device interface 5103 (FIG. 1) and control device interface 5115 (FIG. 1) can manage the extraction from first protocol messages of messages formatted according to the second protocol and insertion of messages formatted according to the second protocol as payload 5517 (FIG. 4A) of messages formatted according to the first protocol. Communications message management can include identifying first protocol messages and extracting tunneled second protocol messages as needed. First protocol messages that include second protocol messages can be processed separately from other messages. First protocol messages can be prepared and queued for transmission separately depending on whether second protocol messages are included. Messages formatted according to the second protocol can include control byte 5521, message ID 5523, data, and CRC 5527 computed over control byte 5521, message ID 5523, and data 5525. Control byte 5521 can be used for message addressing and can include a message sequence number that can be generated by controlled device interface 5103 (FIG. 1) and can be echoed back by control device interface 5115 (FIG. 1). The sequence number can be used by controlled device interface 5103 (FIG. 1) to match a received response message to a sent request message. In some configurations, sequence numbers can begin at 0h, can be incremented after a message is sent, and roll to 0h after Fh. Control byte 5521 can indicate the identification from where a response to the message can be expected. Control byte 5521 can include a processor ID that can identify the processor for which the message is intended.

Continuing to refer to FIG. 4B, message ID 5523 can provide a command and/or an indication of the identity of message data 5525. In some configurations, message ID 5523 can take on the exemplary values in Table I. In some configurations, the sender of the message having message ID 5523 can expect an exemplary response as shown in Table I.

TABLE I

| ID | Message | Expected Response | Payload |
|---|---|---|---|
| 00h | No Message | | |
| 01h | Initialize | 02h | Protocol version # and application ID |
| 02h | Confirm Initialize | N/A | Initialization results and version numbers |
| 03h | Status | N/A | Status code and previous message ID |
| 04h | Resend Last Message | All Msgs | |
| 05h | Communication Complete | 03h | |
| 06h | Get Application CRC | 07h | |

TABLE I-continued

| ID | Message | Expected Response | Payload |
|---|---|---|---|
| 07h | Send Application CRC | N/A | CRC value |
| 10h-2Ah | Controlled device-specific messages | | |
| 2Bh | Set Event Log Status | 2Ch | |
| 2Ch | Send Current Event Log Status | N/A | # event log entries |
| 2Dh | Get Event Segment | 33h | Event index, segment # |
| 2Eh | Clear Events | 03h | |
| 2Fh | Set Alarm Log Status | 30h | |
| 30h | Send Current Alarm Log Status | N/A | # of alarm log entries |
| 31h | Get Alarm Segment | 33h | Alarm index, segment # |
| 32h | Clear Alarms | 03h | |
| 33h | Send Log Segment | N/A | Alarm segment |
| 34h-41h | Controlled device-specific messages | | |
| 42h | Get Real Time Clock | 44h | Clock type ID |
| 44h | Send Real Time Clock-Integer | 03h | Real time clock integer value and clock type ID |
| 45h | Get Serial Number | 46h | Of controlled device |
| 46h | Send Serial Number | 46h | Serial number of controlled device |
| 47h | Get Service Flag | 48h | |
| 48h | Send Service Flag | 48h | Equipment service flag to indicate issues with controlled device |
| 49h-FFh | Controlled device-specific messages | | |

Continuing to refer to FIG. 4B, second protocol messages that can be exchanged can include, but are not limited to including, an initialization message that can be sent from control device 5107 (FIG. 1) to controlled device 5111 (FIG. 1), and an initialization response message that can be sent from controlled device 5111 (FIG. 1) to control device 5107 (FIG. 1). The initialization message can include, but is not limited to including, a protocol map, an application ID, a communication timeout value, and padding. Second protocol messages can include a device control command that can be sent from control device 5107 (FIG. 1) to controlled device 5111 (FIG. 1), and that can include device control information, and padding. Second protocol messages can include commands used to interface with a wireless protocol such as, for example, the BLUETOOTH® protocol, that can enable communications between control device 5107 (FIG. 1) and controlled device 5111 (FIG. 1). The commands can kick off actions such as, for example, scanning for peripherals, discontinuing the scan, retrieving names of peripherals, connecting a peripheral such as, for example, controlled device 5111 (FIG. 1) operating as a peripheral with control device 5107 (FIG. 1), and canceling the peripheral connection. The commands can interrogate peripherals, for example, by discovering services and characteristics of the peripherals, reading and setting values of the characteristics. Responses to the commands can include, but are not limited to including, status updates with respect to peripherals, connections, services, and characteristics.

Referring now primarily to FIGS. 4A and 4B, first protocol commands can include disabling wireless communications in which control device interface 5115 (FIG. 1) can continue operating without control device 5107 (FIG. 1), and in which control device 5107 (FIG. 1) can reactivate if an alarm is received from control device interface 5115 (FIG. 1). Second protocol commands can include commands such as, for example, but not limited to, echo, set/get system events, erase logs, get data, force alarm, set log record on control device 5111 (FIG. 1), force reset of control device 5111 (FIG. 1), startup test for control device 5111 (FIG. 1), integration test commands, and radio service commands. Second protocol commands can include commands such as, for example, but not limited to, set an identification of control device 5111 (FIG. 1), setting of calibration and measurement options, executing of manufacturing tests, and providing a list of events.

Figure 5A:
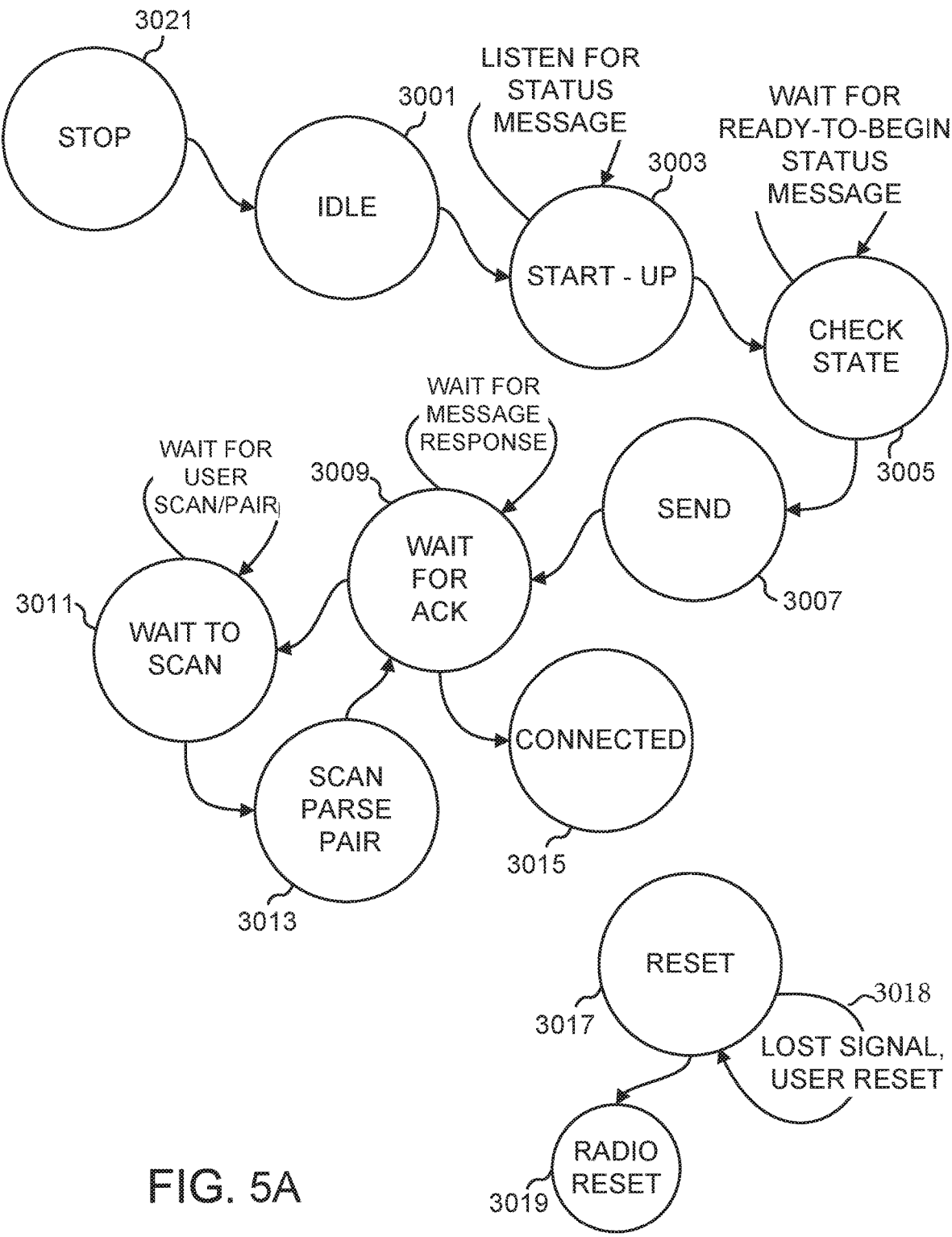
FIGS. 5A and 5B are state diagrams of the communications pairing of the present teachings.

Referring now primarily to FIG. 5A, external application state machine 5305E (FIG. 2) can recognize states such as, for example, but not limited to idle state 3001 in which radio 5331 experiences no activity, and start-up state 3003 in which radio 5331 is started up. In start-up state 3003, external application state machine 5305E (FIG. 2) is set up to listen for a status message from radio 5331 (FIG. 2) that tells external application state machine 5305E (FIG. 2) that radio 5331 (FIG. 2) is ready to begin. In check state 3005, external application state machine 5305E (FIG. 2) awaits the ready-to-begin status message. Other states can include send state 3007 in which external application state machine 5305E (FIG. 2) requests information about dradio 5349 (FIG. 2), for example, but not limited to, its software version number, sends a start radio command to dradio 5349 (FIG. 2), sends a command to dradio 5349 (FIG. 2) to open up pairing with medical device 5111A (FIG. 2), and informs dradio 5349 (FIG. 2) about which of possible medical devices 5111A (FIG. 2) the user has selected. Wait for acknowledgement state 3009 sets external application state machine 5305E (FIG. 2) in a state awaiting a response from the last sent message, for example, but not limited to, acknowledgements concerning radio version number, radio start, pairing, start scan, and parse data. With respect to the parse data acknowledgement, wait for acknowledgement state 3009 informs dradio 5349 (FIG. 2) that a response was received and loops back to the previous state until a pairing is selected or until scanning is stopped. Other responses that can be awaited can include responses to connect messages and connect status messages in which the state is awaiting the successful connection of medical device 5111A (FIG. 2) with the device executing external application 5107A (FIG. 2). Wait to scan state 3011 awaits a command to begin the pairing process and listens for responses from available medical devices 5111A (FIG. 2). Start scan state 3013 sends a command to dradio 5349 (FIG. 2) to start scanning for available medical devices 5111A (FIG. 2) and sets up a state machine to enable the connection in which external application state machine 5305E (FIG. 2) enters connected state 3015. If wireless link 5136 (FIG. 2) is lost, or if message responses time out, or at an external request, external application state machine 5305E (FIG. 2) can enter start reset state 3017 from which radio reset state 3019 can be entered in which a reset command is sent to dradio 5349 (FIG. 2), followed by a wait for response 3018 to the reset command. Stop state 3021 can set up external application state machine 5305E (FIG. 2) to clean up and return to idle state 3001.

Figure 5B:
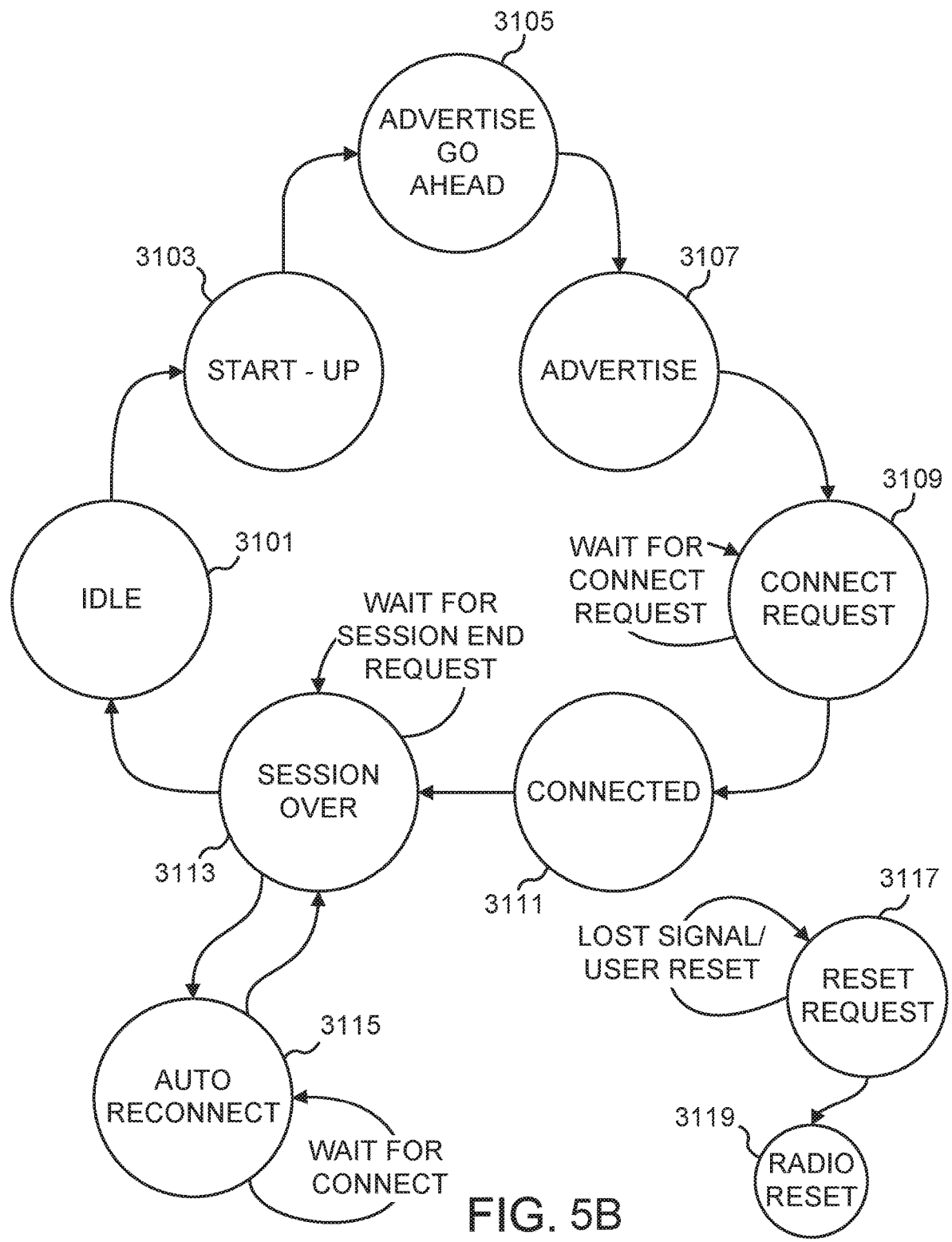

Referring now to FIG. 5B, medical device state machine 5305M (FIG. 2) can include states such as, for example, but not limited to, idle state 3101 in which there is no radio activity, start-up state 3103 in which radio 5331 (FIG. 2) is enabled, advertise go-ahead state 3105 in which medical device 5111A (FIG. 2) receives the go-ahead to advertise the availability of medical device 5111A (FIG. 2) for radio communication, and advertise state 3107 in which identifying information for medical device 5111A (FIG. 2) is made available to listening radios such as, for example, radio 5331 (FIG. 2) associated with external application 5107A (FIG. 2). States can further include waiting for connect request state 3109, accepting a connect request state, connected state 3111 in which medical device 5111A (FIG. 2) can communicate with the desired central radio, and waiting state 3113 in which medical device 5111A (FIG. 2) awaits the end of a wireless session, whether by user action, or loss of radio signal. States can further include reset request state 3117 from which radio 5331 (FIG. 2) can be placed in reset state 3119, and auto-reconnect state 3115 in which radio 5331 (FIG. 2) can attempt to automatically reconnect to the wireless session, depending on how the wireless session ended.

Figure 6A:
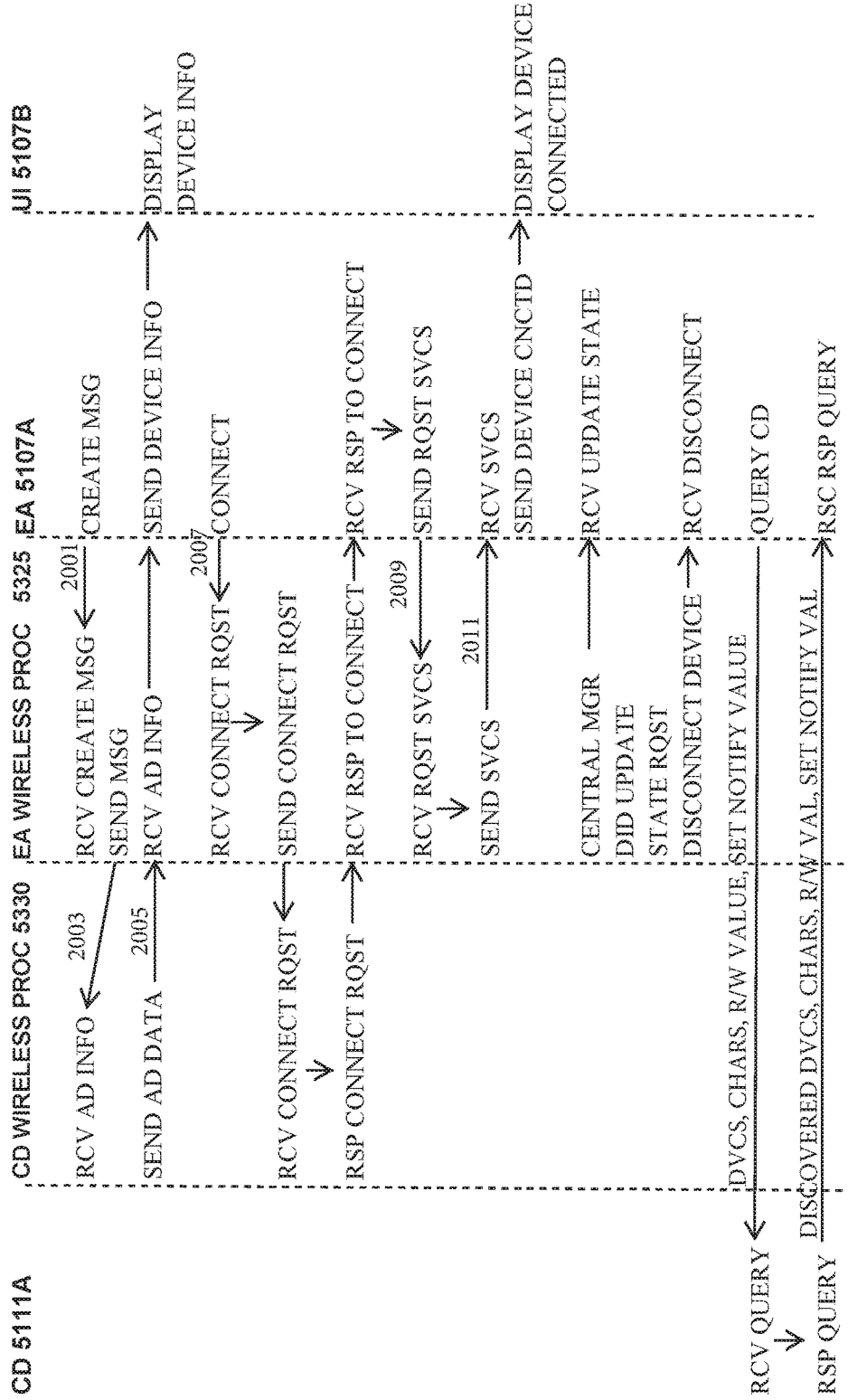
FIGS. 6A and 6B are protocol diagrams of the communications process of the present teachings.

Referring now to FIG. 6A, external application 5107A (FIG. 2) can provide the interface between user interface 5107B executing on an external device and a wireless communications means. In some configurations, the wireless communications means can be based upon the BLUETOOTH® Low Energy protocol, and can include configuring communications between medical device 5111A and external application 5107A, initiating the sending of messages between medical device 5111A and external application 5107A, breaking up of large messages, and enabling device control commands that are initiated by a user of the external device and are transmitted to medical device 5111A. Messages that can be exchanged can include, but are not limited to including, scan for devices, stop scan, and retrieve devices, where devices can include medical device 5111A. Medical device 5111A and external application 5107A can communicate with wireless processors 5325/5330 that can manage the transmission and reception of messages between external application 5107A and medical device 5111A. External application 5107A can create message 2001 using, for example, but not limited to, an applications program interface that can communicate with external application wireless processor 5325, which can receive create message 2001, and use the information from create message 2001 to build and send advertising information 2003 to medical device wireless processor 5330. Advertising information 2003 can include, but is not limited to including, company identification, project identification, and customer identification. Medical device wireless processor 5330 can use advertising information 2003 to build and send advertising data 2005 through external application wireless processor 5325 to external application 5107A, which can build and send device information to user interface 5107B to display on the external device. External application 5107A can send connect request 2007 to external application wireless processor 5325, which can build and send a connect request to medical device wireless processor 5330. Medical device wireless processor 5330 can respond to the connect request through external application wireless processor 5325 to external application 5107A, which can react to the response by sending service request 2009 to external application wireless processor 5325, which can respond by sending services 2011 to external application 5107A. Connect request 2007 can include commands to connect medical device 5111A and/or cancel the connection to medical device 5111A. The response to connect request 2007 can include success or failure notifications. External application 5107A can receive services 2011 and notify external device user interface 5107B that the device is connected. As communications start-up is in progress, a central manager within external application wireless processor 5325 can update the state of external application wireless processor 5325 and send the updated state information to external application 5107A. A disconnect request and response could be exchanged while communications are in progress, and external application wireless processor 5325 can provide the disconnect request to external application 5107A. As communications start-up is in progress, external application 5107A can query medical device 5111A by sending messages such as, for example, but not limited to, discovering the services and characteristics of medical device 5111A, and requesting reading and writing values from/to medical device 5111A. The query can be answered by a response that can provide data and status of medical device 5111A.

Figure 6B:
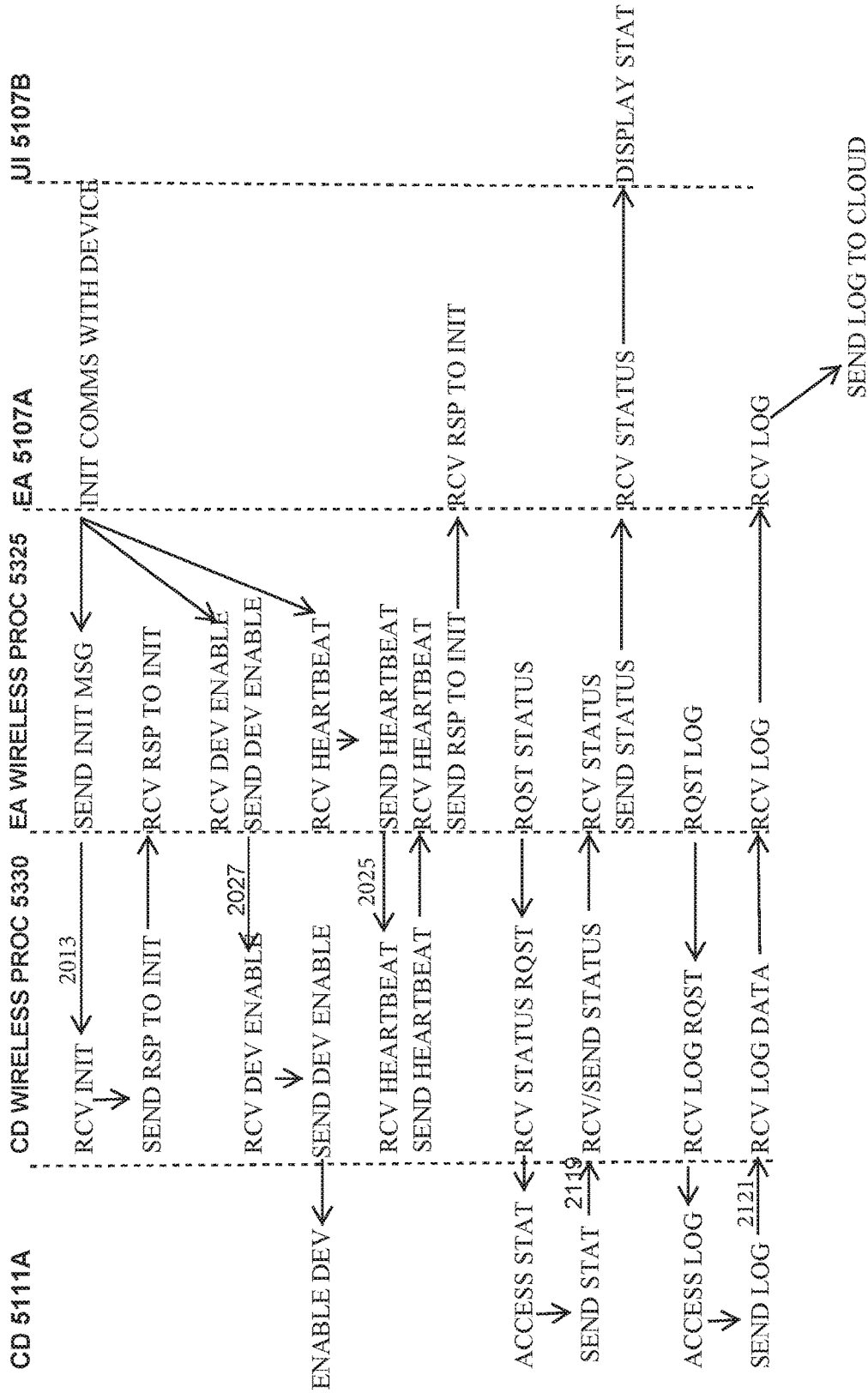

Referring now to FIG. 6B, following communications start-up, external application 5107A can initiate communications with medical device 5107A by commanding external application wireless processor 5325 to send initialization message 2013, send device enable message 2027, and send heartbeat message 2025 to medical device wireless processor 5330. Medical device wireless processor 5330 can receive device enable message 2027 and notify medical device 5111A that the device control of external application 5107A is enabled. External application wireless processor 5325 can request, through medical device wireless processor 5330, a status of medical device 5111A. Medical device 5111A can receive the status request, access the status, and send status message 2119 through medical device wireless processor 5330 and external application wireless processor 5325 to external application 5107A, which can provide the status to external device user interface 5107B. External application wireless processor 5325 can request, through medical device wireless processor 5330, a log from medical device 5111A. Medical device 5111A can receive the log request, access the log, and send log message 2121 through medical device wireless processor 5330 and external application wireless processor 5325 to external application 5107A, which can provide the log to an external storage device.

Figure 7:
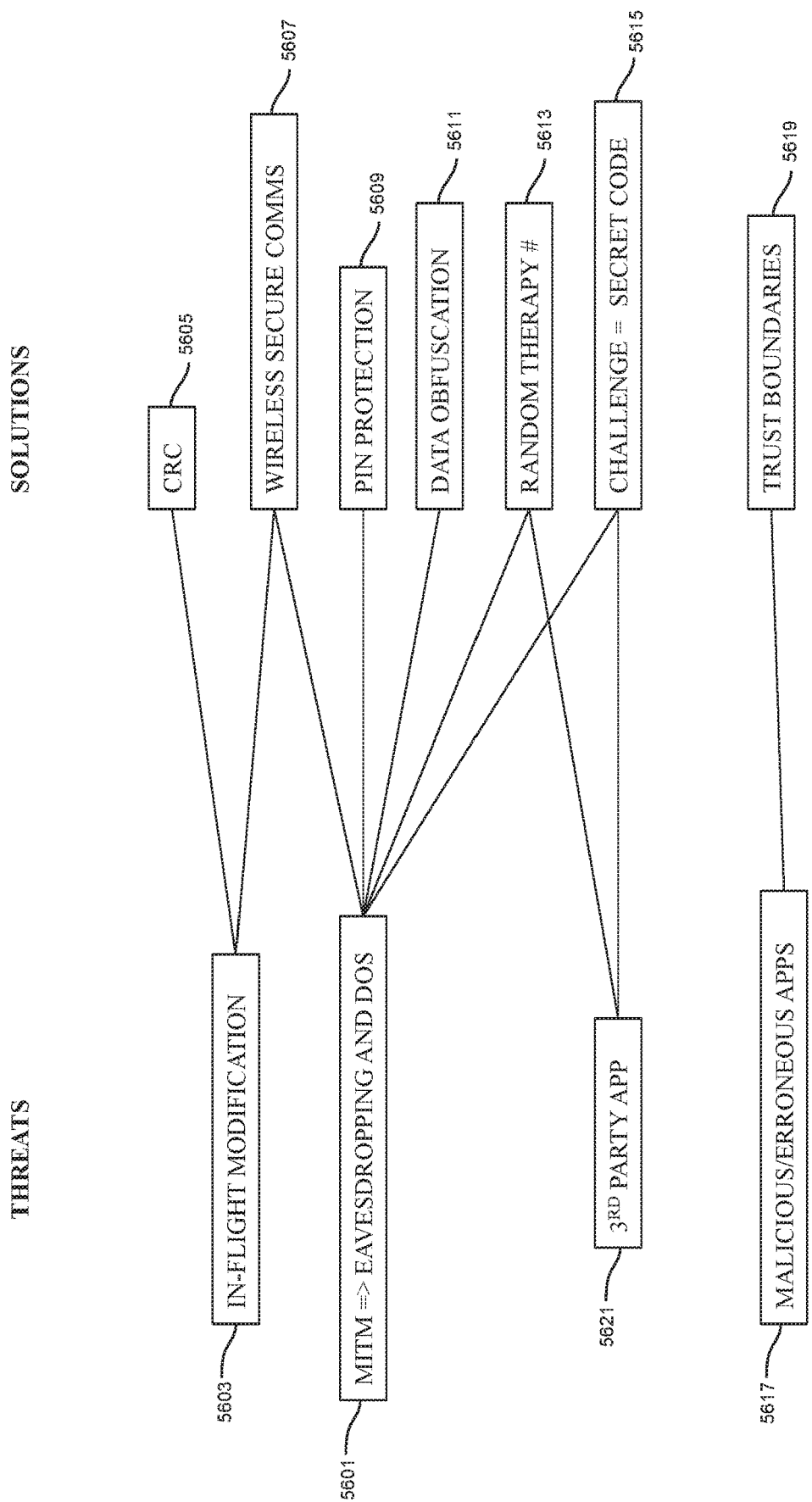
FIG. 7 is a schematic block diagram of a set of threats that can be encountered by the system of the present teachings.

Referring to FIG. 7, there can be several ways that the security of controlled device 5111 (FIG. 1) can be compromised. External communications and internal controls can be explicitly or accidentally exploited causing minor to catastrophic results. Identifying specific ways that the exploitation, referred to herein as threats, can occur and be mitigated can be done by analyzing points where attacks can occur in communications and controls of controlled device 5111 (FIG. 1). The sum of the points can be referred to as the attack surface. The objective of making controlled device 5111 (FIG. 1) more secure can be achieved by reducing the size of the attack surface as much as possible, for example, by reducing the number of points. Remaining points can be mitigated. The resulting risk to controlled device 5111 (FIG. 1) can be quantified by assigning severity scores to the points where attacks can occur. This can be done by, for example, but not limited to, assessment tools such as Common Vulnerability Scoring System (CVSS). With respect to threat analysis, external communications can be put at risk through, for example, but not limited to, malicious modification threats 5603 of message traffic, eavesdropping and replay threats 5601, and co-opting control threats 5621 of control device interface 5115 (FIG. 1). Internal control compromises can include, but are not limited to including, malicious and/or erroneous applications 5617 that can cause intended and/or unintended results that can compromise security of controlled device 5111 (FIG. 1). In-flight modification 5603 of message traffic can be detected by standard procedures that can be available in commercial wireless products 5607 such as, for example, but not limited to, products that adhere to the BLE standard in which a secure link can be established using Elliptic Curve Diffie-Hellman key exchange and AES-128 encryption. CRC protection 5605 can also be used to detect in-flight threats.

Continuing to refer to FIG. 7, with respect to man-in-the-middle (MitM) threats 5601, when wireless devices are first paired, an attacker can place itself "in the middle" of the connection. Two valid but separate wireless encrypted connections can be established with a bad actor placing itself in the middle and reading or modifying unencrypted clear text that can be available between the two encrypted connections. MitM attacks 5601 can include an attacker's monitoring messages, and altering and/or injecting messages into a communication channel. One example is active eavesdropping, in which the attacker makes independent connections with the victims and relays messages between them to make them believe they are talking directly to each other over a private connection, when in fact the entire conversation is controlled by the attacker. The attacker can intercept messages passing between the two victims and inject new ones. The victim(s) can also be subject to a replay attack in which the MitM records traffic and inserts new messages containing the same text, and then continually plays the messages back. Standard security features of commercial wireless protocols 5607, such as, for example, authentication, confidentiality, and authorization, can thwart some types of MitM attacks 5601. Authentication can include verifying the identity of communicating devices based on their device addresses. Confidentiality can include protecting information from eavesdropping by ensuring that only authorized devices can access and view transmitted data. Authorization can include insuring that a device is authorized to use a service. MITM threats 5601 can be thwarted by using a passkey entry pairing method, an out of band pairing method, or a numeric comparison method.

Continuing to refer to FIG. 7, personal identification number (PIN) protection 5609 from MitM threats 5601 can include the exchange of a code, for example a six-digit code, between control device interface 5115 (FIG. 1) and control device 5107 (FIG. 1) using a short-term key. The six-digit code can be exchanged one bit at a time, and both sides must agree on the bit setting before another bit can be exchanged. At pairing time, control device 5107 (FIG. 1) can request entry of a six-digit code that can be physically located on control device interface 5115 (FIG. 1), and control device interface 5115 (FIG. 1) can respond with the same six-digit code. MitM threats 5601 have no access to the six-digit code physically located on control device interface 5115 (FIG. 1) and can therefore not assume control of control device interface 5115 (FIG. 1) from control device 5107 (FIG. 1). The pairing mechanism is the process in which control device 5107 (FIG. 1) and control device interface 5115 (FIG. 1) exchange identity information that paves the way for setting up encryption keys for future data exchange.

Continuing to refer to FIG. 7, anyone who buys a complete system as shown in FIG. 1 can know the controlled device PIN and can stage MitM attacks 5601. The MitM can operate the system and figure out the first protocol. Or the MitM could grab the message traffic between control device 5107 (FIG. 1) and control device interface 5115 (FIG. 1) and learn the first protocol. Or the MitM could examine internal electrical busses of control device interface 5115 (FIG. 1) to capture the first protocol traffic and figure out the first protocol. Clear text obfuscation 5611 can thwart these types of threats. Clear text obfuscation 5611 can include randomizing clear text so that even if the same message is sent repeatedly, the eavesdropped version varies randomly. Either of control device 5107 (FIG. 1) or control device interface 5115 (FIG. 1) can obfuscate the clear text in the message before transmitting the message, and either of control device interface 5115 (FIG. 1) or control device 5107

(FIG. 1) can deobfuscate the clear text. Once obfuscated, the messages appear to be random lengths and appear to contain random data and the clear text cannot be seen outside of the control device interface 5115 (FIG. 1) or control device 5107 (FIG. 1). The obfuscation algorithm on control device 5107 (FIG. 1) can be kept secret through a security feature such as, for example, Licel's DexProtector tool. The obfuscation algorithm can be kept secret on control device interface 5115 (FIG. 1) by setting the radio processor in control device interface 5115 (FIG. 1) to disallow readback of the code and access to debugging features. In some configurations, the obfuscation algorithm can be "stateless" in that transmitted messages can be recovered independently of any previous message traffic, obviating the need to maintain any shared state between the sender and the receiver. In some configurations, even for clear text that is a series of messages of the same length, the length of the obfuscated messages can vary randomly. In some configurations, a first number of bytes of every message can be random. In some configurations, the algorithm can execute without read only memory (ROM) for data tables and with a relatively small amount of rapid access memory (RAM), code, and compute cycles.

Continuing to refer to FIG. 7, in some configurations, trust boundary 5619 can be maintained between control device 5107 (FIG. 1) and network storage 5113 (FIG. 1). Trust boundaries 5619 are the places where the location of data associated with a system can create potential opportunities for trust violations, for example, if the data are outside the control of control device 5107 (FIG. 1) and/or controlled device 5111 (FIG. 1), or where the data leave the external application infrastructure. Trust can be maintained through the exchange of keys and encryption of messages between, for example, control device 5107 (FIG. 1) and network storage 5113 (FIG. 1). Trust boundary 5619 can exist between control device 5107 (FIG. 1) and controlled device 5115 (FIG. 1). Trust can be maintained across this interface through the use of BLE secure communications and PIN bonding with controlled device 5111 (FIG. 1). In some configurations, trust boundaries 5619 can occur within control device 5107 (FIG. 1), between, for example, external application 5107A (FIG. 2) and system services. Trust can be established by the use of a key and sandboxing on control device 5107 (FIG. 1) to keep data safe from other applications. In some configurations, databases can be protected by file encryption, protecting the data files with file system encryption tied to the application keys. Trust can be maintained through the exchange of keys and encryption of messages between control device 5107 and network storage 5113.

Figure 8:
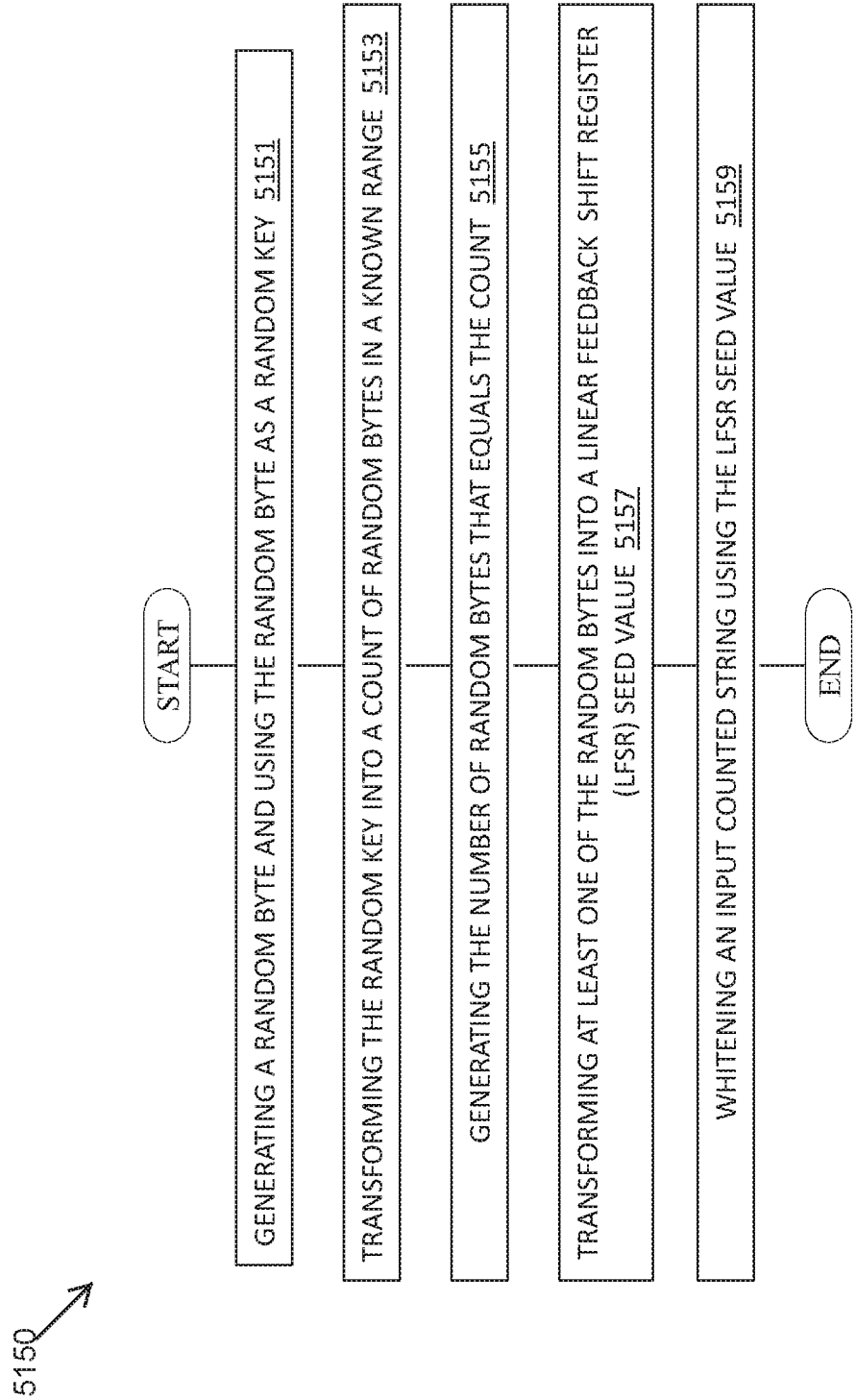
FIG. 8 is a flowchart of the method of clear text obfuscation of the present teachings.

Referring now to FIG. 8, method 5150 for obfuscating plain text can include, but is not limited to including, generating 5151 a random byte and using the random byte as a random key, transforming 5153 the random key into a count of random bytes in a known range, generating 5155 the number of random bytes that equals the count, and transforming 5157 several of the random bytes into a linear feedback shift register (LFSR) seed value. Method 5150 can include whitening 5159 an input counted string using the LFSR seed value.

Figure 9:
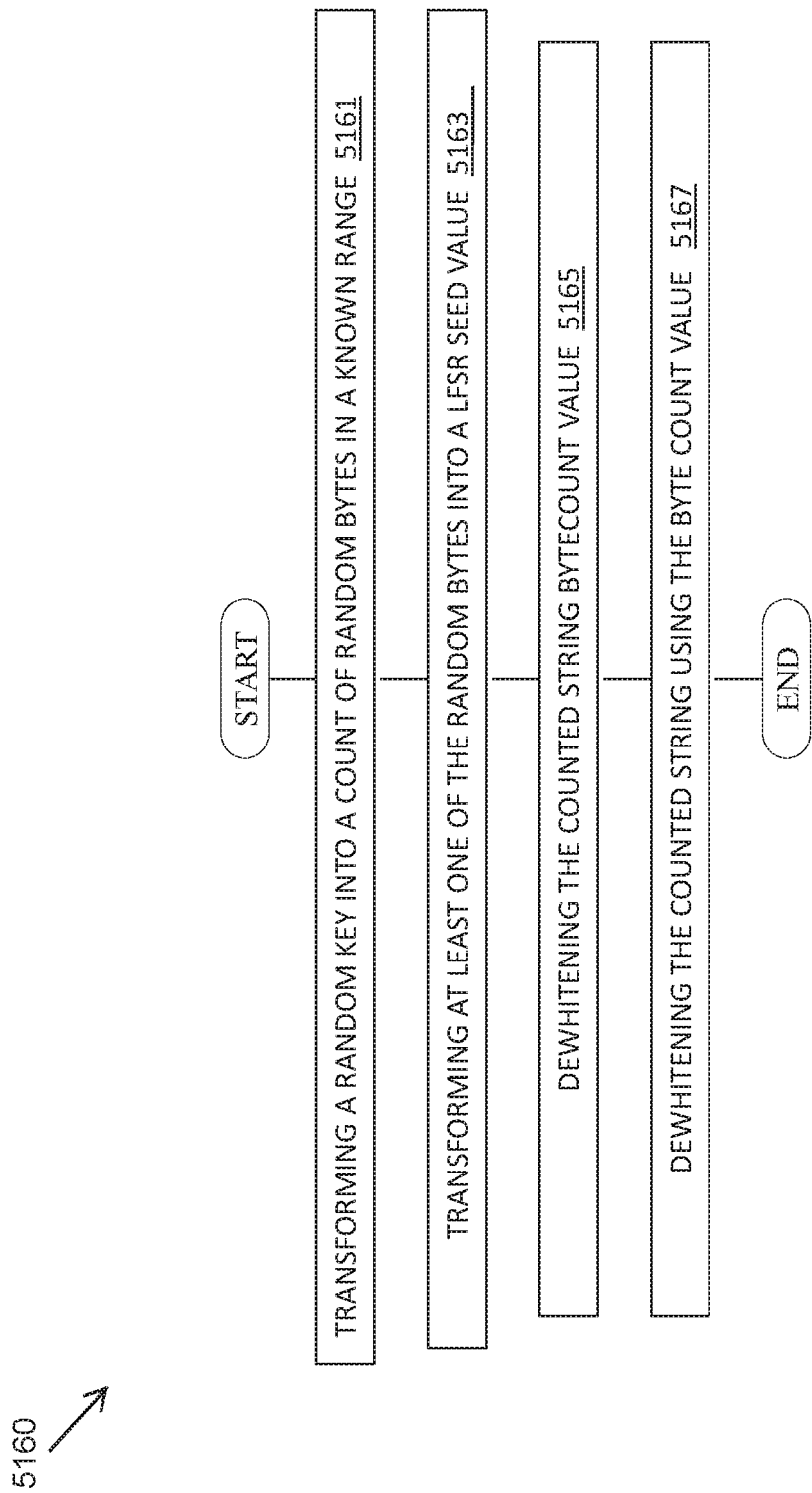
FIG. 9 is a flowchart of the method of clear text deobfuscation of the present teachings.

Referring now to FIG. 9, method 5160 for deobfuscating the clear text can include, but is not limited to including, transforming 5161 the random key into the count of random bytes in the known range, transforming 5163 several of the random bytes into the LFSR Seed value, dewhitening 5165 the original counted string byte count value, dewhitening 5167 the counted string using the byte count value.

Referring again to FIG. 7, the MitM can record a message between control device 5107 (FIG. 1) and control device interface 5115 (FIG. 1) and can replay it incessantly. If control device 5111 (FIG. 1) is a medical device, a random therapy message number transmitted by controlled device can thwart replay attacks because control device 5107 (FIG. 1) must reiterate the random therapy message number with a next command message. If control device 5107 (FIG. 1) does not include the random therapy message number, controlled device can reject the message, thereby preventing replaying the same message repeatedly.

Figure 10:
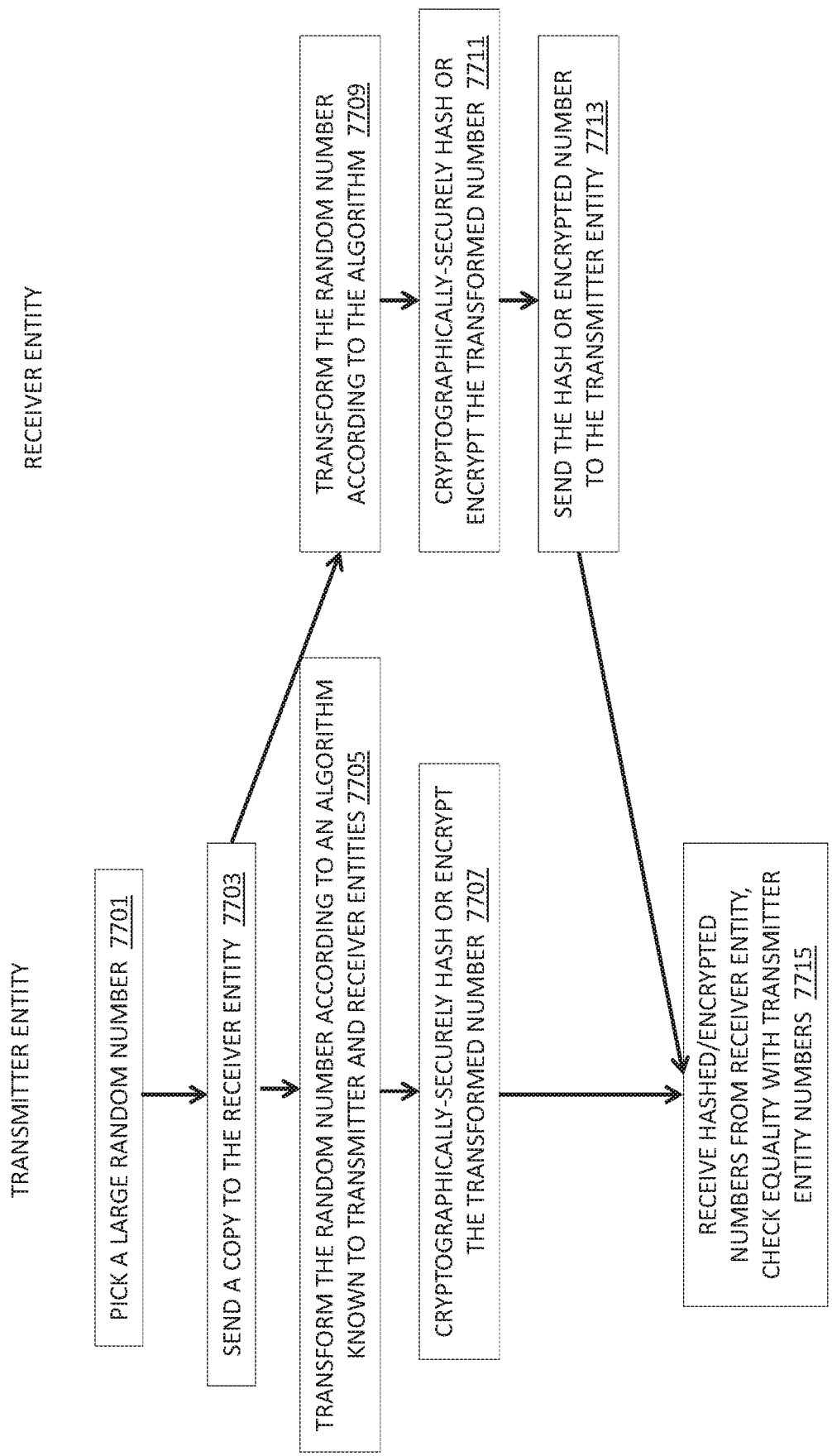
FIG. 10 is a schematic block diagram of the challenge-response authentication process of the present teachings.

Referring now to FIG. 10, since anybody who has a wireless device that can communicate according to the wireless protocol used between control device 5107 (FIG. 1) and control device interface 5115 (FIG. 1) can hack in between control device interface 5115 (FIG. 1) and control device 5107 (FIG. 1), challenge/response process 5615 can be used to thwart malicious actors. For example, if a third party application becomes readily available, for example, for sale on mobile devices in application stores, control device interface 5115 (FIG. 1) or control device 5107 (FIG. 1), either acting as sender, can present a challenge to control device 5107 (FIG. 1) or control device interface 5115 (FIG. 1), either acting as receiver, and the receiver must present the correct response. The method, from the point of view of the sender, for thwarting security threats by challenge/response can include, but is not limited to including, picking 7701 a large random number, sending 7703 the large random number to a receiver, and transforming 7705/7709, by the sender and the receiver, the large random number in the same secret way. The method can include hashing or encrypting 7707/7711, by the sender and the receiver, the transformed number in a cryptographically-secure way, receiving 7713, from the receiver, the hashed or encrypted number, and checking 7715 that the number hashed or encrypted by the sender and the number hashed or encrypted by the receiver are equal. The challenge/response process can rely on both sender and receiver using the same secret transform algorithm. At no time does the transformed number travel over the radio in an unencrypted fashion, protecting the secret transform. To keep the algorithm secret, a controller can use commercially-available tools such as, for example, but not limited to, Licel's DEXProtector, that can provide, for example, string, class, and resource encryption, integrity control, and hiding of application programming interfaces.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of the system can operate on a computer having a variable number of CPUs. Other alternative computer platforms can be used.

The present configuration is also directed to software for accomplishing the methods discussed herein, and computer readable media storing software for accomplishing these methods. The various modules described herein can be accomplished on the same CPU, or can be accomplished on different computers. In compliance with the statute, the present configuration has been described in language more or less specific as to structural and methodical features. It is to be understood, however, that the present configuration is not limited to the specific features shown and described, since the means herein disclosed comprise preferred forms of putting the present configuration into effect.

Methods can be, in whole or in part, implemented electronically. Signals representing actions taken by elements of the system and other disclosed configurations can travel over at least one live communications network. Control and data information can be electronically executed and stored on at least one computer-readable medium. The system can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific configurations, it is to be understood that they are not limited to these disclosed configurations. Many modifications and other configurations will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A method for securely remotely controlling a medical device with a control device, the medical device and the control device being coupled by a communications link, the control device including a control messaging system, the medical device including a medical device messaging system, the method comprising:
preparing a device-specific message based on a current medical device state of the medical device, the device-specific message being prepared by the medical device messaging system including at least one medical device state machine, the at least one medical device state machine including the current medical device state, the device-specific message being encapsulated in a second communications protocol having a control byte, a message identification, and a second error checking means, the message identification being associated with the medical device;
preparing a communications message based on a current control state, the communications message being prepared by the control messaging system including at least one control state machine, the at least one control state machine including the current control state, the communications message including a first communications protocol, the first communications protocol including driver bytes, a header, and a first error checking means, the driver bytes, the header and the first error checking means encapsulating the device-specific message and the second communications protocol;
queuing, by the control device, the communications message based on the current control state;
dequeuing, by the control communications system, the communications message based on the current control device communications state;
applying, by the control communications system, communications threat control to the communications message by obfuscating clear text data in the communications message to obtain a threat controlled communications message including:
generating a random byte;
using the random byte as a random key;
transforming the random key into a first count of random bytes in a known range;
generating a number of random bytes that equals the first count;
transforming several of the random bytes into a linear feedback shift register (LFSR) seed value; and
whitening an input counted string of the clear text data using the LFSR seed value forming obfuscated clear text data in the communications message;
transmitting, by the control communications system, the threat controlled communications message based on the current control communications state;
receiving, by the medical device communications system, a message based on the current medical device communications state;
verifying, by the medical device communications system, based on the communications threat control and the current medical device state, that the received message is the same as the threat controlled communications message;
deobfuscating the obfuscated clear text data including:
transforming the random key into a second count of random bytes in a known range;
transforming at least one of the random bytes into the LFSR seed value;
dewhitening the second count of random bytes; and
dewhitening the whitened input counted string using the dewhitened second count of random bytes and the LFSR seed value;
queuing, by the medical device communications system, the verified received message;
dequeuing, by the medical device, based on the current medical device state, the verified received message; and
controlling the medical device based on the device-specific message included in the verified received message and the current medical device state.

2. The method as in claim 1 wherein the communications system comprises wireless communications between the control device and the medical device.

3. The method as in claim 1 wherein the first communications protocol comprises a remote interface specification protocol.

4. The method as in claim 1 wherein the second communications protocol comprises a service component architecture (SCA) protocol.

5. The method as in claim 1 wherein the communications threat control comprises a challenge-response authentication process.

6. The method as in claim 5 wherein the challenge-response authentication process comprises:
  picking, by a transmitting entity, a random number;
  sending, by the transmitting entity, the random number to a receiver;
  transforming, by the transmitting entity and by a receiving entity, the random number according to an algorithm known to the transmitting entity and the receiving entity;
  cryptographically securely processing, by the transmitting entity and the receiving entity, the transformed number, creating a receiver processed number and a transmitter processed number;
  sending, by the receiving entity, the receiver processed number;
  receiving, by the transmitting entity, the receiver processed number; and
  checking, by the transmitting entity, that the receiver processed number and the transmitter processed number are equal.

7. The method as in claim 6 wherein the cryptographically secure processing comprises hashing.

8. The method as in claim 6 wherein the cryptographically secure processing comprises encryption.

9. A system for securely remotely controlling a medical device comprising:
  a configuration processor configuring a communications system between a control device and the medical device, the communications system including a control communications state machine and a medical device communications state machine, the control communications state machine including a current control communications state, the medical device communications state machine including a current medical device communications state, the configuration processor configuring a control messaging system at the control device, the control messaging system including at least one control state machine, the at least one control state machine including a current control state, the configuration processor configuring a medical device messaging system at the medical device, the medical device messaging system including at least one medical device state machine, the at least one medical device state machine including a current medical device state;
  a message processor preparing a device-specific message based on the current medical device state, the device-specific message being encapsulated in a second communications protocol having a control byte, a message identification, and a second error checking means, the message identification being associated with the medical device, the message processor preparing a communications message based on the current control state, the communications message including a first communications protocol, the first communications protocol including driver bytes, a header, and a first error checking means, the driver bytes, the header and the first error checking means encapsulating the device-specific message and the second communications protocol, the message processor queuing, by the control device, the communications message based on the current control state, the message processor dequeuing, by the control communications system, based on the current control device communications state, the communications message, and applying, by the control communications system, communications threat control to the communications message,
  the communications threat control including obfuscation, by the control device, of clear text data in the communications message to obtain a threat controlled communication message and encrypted data deobfuscation, by the medical device, of the obfuscated clear text data, the clear text data obfuscation including a first process generating a random byte, using the random byte as a random key, transforming the random key into a first count of random bytes in a known range, generating a number of random bytes that equals the first count, and transforming several of the random bytes into a linear feedback shift register (LFSR) seed value, the first process further comprises whitening an input counted string of the clear text data using the LFSR seed value, the encrypted data deobfuscation including a second process transforming the random key into a second count of random bytes in a known range, transforming at least one of the random bytes into the LFSR seed value, dewhitening the second count of random bytes, and dewhitening the whitened input counted string using the dewhitened second count of random bytes and the LFSR seed value;
  a communications processor transmitting, by the control communications system, based on the current control communications state, the threat controlled communications message, the communications processor receiving, by the medical device communications system, based on the current medical device communications state, a message;
  a threat processor verifying, by the medical device communications system, based on the communications threat control and the current medical device state, that the received message is the same as the threat controlled communications message, the threat processor queuing, by the medical device communications system, the verified message; and
  a control processor dequeuing, by the medical device, based on the current medical device state, the verified message, the control processor controlling the medical device based on the device-specific message and the current medical device state.

10. The system as in claim 9 wherein the communications system comprises wireless communications between the control device and the medical device.

11. The system as in claim 9 wherein the second communications protocol comprises a service component architecture (SCA) protocol.

12. The system as in claim 9 wherein the communications threat control comprises clear text data obfuscation and encrypted data deobfuscation.

13. The system as in claim 9 wherein the communications threat control comprises a challenge-response authentication.

14. The system as in claim 13 wherein the challenge-response authentication comprises a third process picking, by a transmitting entity, a random number, sending, by the transmitting entity, the random number to a receiver, transforming, by the transmitting entity and by a receiving entity, the random number according to an algorithm known to the transmitting entity and the receiving entity, cryptographically securely processing, by the transmitting entity and the receiving entity, the transformed number, creating a receiver processed number and a transmitter processed number, sending, by the receiving entity, the receiver processed number, receiving, by the transmitting entity, the receiver processed number, and checking, by the transmitting entity, that the receiver processed number and the transmitter processed number are equal.

15. The system as in claim 14 wherein the cryptographically secure processing comprises hashing.

16. The system as in claim 14 wherein the cryptographically secure processing comprises encryption.

* * * * *